United States Patent
Yano

(10) Patent No.: US 10,357,478 B2
(45) Date of Patent: Jul. 23, 2019

(54) POLYAMIDE COMPOUND AND PHARMACEUTICAL COMPOSITION FOR TREATING MITOCHONDRIAL GENETIC DISEASES

(71) Applicant: Triplex Therapeutics Inc., Chiba (JP)

(72) Inventor: Takamitsu Yano, Ibaraki (JP)

(73) Assignee: TRIPLEX THERAPEUTICS INC., Chiba (JP)

( * ) Notice: Subject to any disclaimer, the term of this patent is extended or adjusted under 35 U.S.C. 154(b) by 65 days.

(21) Appl. No.: 15/357,335

(22) Filed: Nov. 21, 2016

(65) Prior Publication Data

US 2017/0071912 A1 Mar. 16, 2017

Related U.S. Application Data

(62) Division of application No. 14/008,982, filed as application No. PCT/JP2012/058957 on Apr. 2, 2012, now Pat. No. 9,518,152.

(30) Foreign Application Priority Data

Mar. 31, 2011 (JP) ................. 2011-080804

(51) Int. Cl.

| A61K 31/4178 | (2006.01) |
|---|---|
| C07D 403/14 | (2006.01) |
| A61K 31/785 | (2006.01) |
| A61K 31/787 | (2006.01) |
| C08G 73/06 | (2006.01) |
| C12N 15/10 | (2006.01) |
| A61K 47/59 | (2017.01) |

(52) U.S. Cl.
CPC ........ *A61K 31/4178* (2013.01); *A61K 31/785* (2013.01); *A61K 31/787* (2013.01); *C07D 403/14* (2013.01); *C08G 73/0611* (2013.01); *C08G 73/0616* (2013.01); *A61K 47/595* (2017.08); *C12N 15/1062* (2013.01); *C12Q 2600/178* (2013.01)

(58) Field of Classification Search
CPC ............................. A61K 31/787; A61K 47/595
See application file for complete search history.

(56) References Cited

U.S. PATENT DOCUMENTS

| 7,915,233 B1 | 3/2011 | Von Borstel |
|---|---|---|
| 2001/0005719 A1 | 6/2001 | Von Borstel |
| 2001/0016576 A1 | 8/2001 | Von Borstel |
| 2002/0049182 A1 | 4/2002 | Von Borstel et al. |
| 2005/0070606 A1 | 3/2005 | Mori et al. |
| 2005/0203066 A1 | 9/2005 | Von Borstel |
| 2007/0010479 A1 | 1/2007 | Von Borstel |
| 2009/0042965 A1 | 2/2009 | Dervan |
| 2009/0118257 A1 | 5/2009 | Jankowski et al. |
| 2011/0144051 A1 | 6/2011 | Von Borstel |
| 2012/0122934 A1 | 5/2012 | Jankowski et al. |

FOREIGN PATENT DOCUMENTS

| JP | 2004538326 A | 12/2004 |
|---|---|---|
| JP | 2011503005 A | 1/2011 |
| WO | 2003068215 A1 | 8/2003 |

OTHER PUBLICATIONS

International Search Report for PCT/JP2012/058957 dated Apr. 10, 2012.
Yano; "MELAS A3243G Hen'i-gata Mitochondria DNA to Mitochondria Tensha Shuketsu Inshi mTERF no Kino Mechanism," 2010 Nendo Gakui Ronbun (Hakushi) pp. 7-10 and 57-101.
Shaag, A et al; "Mitochondrial encephalomyopathy associated with a novel mutation in the mitochondrial tRNALeu (UUR) gene (A3243T)," 1997, Biochemical and Biophysical Research Communications, vol. 233, No. 3, p. 637-639.
Seneca S et al; "A new mitochondrial point mutation in the transfer RNALeu gene in a patient with a clinical phenotype resembling Kearns-Sayre syndrome," 2001, Archives of Neurology, vol. 58, p. 1113-1118.
Bosley, T.M. et al; Sporadic bilateral optic neuropathy in children: the role of mitochondrial abnormalities, 2008, Investigative Ophthalmology and Visual Science, vol. 49, No. 12, p. 5250-5256.
Goto Y et al; A novel point mutation in the mitochondrial tRNALeu(UUS) gene in a family with mitochondrial myopathy, 1992, Annals of Neurology, vol. 31, No. 6, p. 672-675.
Chen Y et al; Mitochondrial gene mutations in gestational diabetes mellitus, 2000, Diabetes Research and Clinical Practice, vol. 48, No. 1, p. 29-35.
Nishigaki Y et al; 37 A novel mitochondrial tRNALeu(UUR) mutation in a patient with features of MERRF and Kearns-Sayre syndrome, 2003, Neuromuscular Disorders, vol. 13, No. 4, p. 334-340.
Mariotti C et al; 37 Defective respiratory capacity and mitochondrial protein synthesis in transformant cybrids harboring the tRNALeu(UUR) mutation associated with maternally inherited myopathy and cardiomyopathy, 1994, Journal of Clinical Investigation, vol. 93, No. 3, p. 1102-1107.

(Continued)

*Primary Examiner* — Gregory Listvoyb
(74) *Attorney, Agent, or Firm* — Heslin Rothenberg Farley & Mesiti P.C.

(57) ABSTRACT

The object of the present invention is to provide a fundamental therapy to mitochondrial genetic diseases caused by mutation of the mitochondrial (mt)DNA, and a pharmaceutical composition used for the same.
The object can be solved by a polyamide compound binding to a target double-stranded mtDNA comprising A/T pair consisting of first A of the following sense-stranded DNA and the corresponding T, A/T pair consisting of 8th A of the following sense-stranded DNA and the corresponding T, G/C pair consisting of 9th G of the following sense-stranded DNA and the corresponding C, G/C pair consisting of 14th G of the following sense-stranded DNA and the corresponding C, T/A pair consisting of 15th T of the following sense-stranded DNA and the corresponding A, or the like, in the double-stranded DNA consisting of the sense-stranded DNA having base sequence of 5'-ATGGCAGAGCCCGG-TAATCGCATAA-3' (SEQ ID NO: 1) and the antisense-stranded DNA having base sequence of 5'-TTATGCGAT-TACCGGGCTCTGCCAT-3' (SEQ ID NO: 2).

14 Claims, 6 Drawing Sheets
Specification includes a Sequence Listing.

(56) References Cited

OTHER PUBLICATIONS

Houshmand L et al; 37 Fatal mitochondrial myopathy, lactic acidosis, and complex I deficiency associated with a heteroplasmic A-G mutation at position 3251 in the mitochondrial tRNALeu(UUR) gene, 1996, Human Genetics, vol. 97, No. 3, p. 269-273.

Taylor et al; "Selective inhibition of mutant human mitochondrial DNA replication in vitro by peptide nucleic acids," Nature Genetics, Britain, 1997, vol. 15, pp. 212-215.

Taylor et al; "An antigenomic strategy for treating heteroplasmic mtDNA disorders," Advanced Drug Delivery Reviews, Netherlands, 2001, vol. 49, pp. 121-125.

Hyvarinen et al., The Mitochondrial transcription termination factor mTERF modulates replication pausing in human imtochondrial DNA, Nucleic Acids Research vol. 35, No. 19, Sep. 20, 2007.

Yano et al., Loss of Mutant Mitochondrial DNA harboring the MELAS A3243G Mutation in Human Cybrid Cells After Cell-Cell Fusion with Normal Tissue-Derived Fibroblast Cells, International Journal of Molecular Medicine 25, 2010.

Farkas, Structural Variations on the Turn Unit of DNA-Binding Hairpin Py-Im Polyamides, Ph.D. Thesis, California Institute of Technology, Jan. 2010.

USPTO Structure Search, dated Oct. 2015.

Supplemental European Search Report in European Patent Application No. 1276514=51.1, dated Jun. 10, 2014.

Muratovska, et al., Targeting Peptide Nucleic Acid (PNA) Oligomers to Mitchondria Within Cells by Conjugation To Lipophilic Cations: Implications for Mitochondrial DNA Replication, Expression and Disease, vol. 29, No. 9, 2001, Oxford University Press, Received Jan. 31, 2001 and Accepted Mar. 7, 2001.

Normal-type (Wild-type)

```
5'-ATGGCAGAGCCCGGTAATCGCATAA-3'
3'-TACCGTCTCGGGCCATTAGCGTATT-5'
```

(a1)
```
5'-TGGCAGAG-3'
3'-ACCGTCTC-5'
```

(a2)
```
5'-TGGCAGAGCCG-3'
3'-ACCGTCTCGGG-5'
```

(a3)
```
5'-TGGCAGAGCCCG-3'
3'-ACCGTCTCGGGC-5'
```

(b1)
```
5'-AGCCCGGT-3'
3'-TCGGGCCA-5'
```

(b2)
```
5'-AGCCCGGTA-3'
3'-TCGGGCCAT-5'
```

(c1)
```
5'-TGGCAGA-3'
3'-ACCGTCT-5'
```

(c2)
```
5'-ATGGCAGA-3'
3'-TACCGTCT-5'
```

(d1)
```
5'-TAATCGCAT-3'
3'-ATTAGCGTA-5'
```

(e1)
```
5'-AATCGCATA-3'
3'-TTAGCGTAT-5'
```

(f1)
```
5'-TCGCATAA-3'
3'-AGCGTATT-5'
```

FIG. 2

POLYAMIDE COMPOUND AND PHARMACEUTICAL COMPOSITION FOR TREATING MITOCHONDRIAL GENETIC DISEASES

CROSS REFERENCE TO RELATED APPLICATIONS

This application is a continuation of U.S. Non-Provisional application Ser. No. 14/008,982, filed on Sep. 30, 2013, which is a national stage filing under section 371 of International Application No. PCT/JP2012/058957 filed Apr. 2, 2012 and published as WO/2012/133896, and claims priority to Japanese Patent Application No. 2011-080804 filed on Mar. 31, 2011, the entire disclosure of these applications being hereby incorporated herein by reference.

REFERENCE TO A SEQUENCE LISTING

This application contains a sequence listing, provided as a paper copy, as required under 37 C.F.R. § 1.821(c), and is herein incorporated by reference in its entirety, as required under 37 C.F.R. § 1.52(e)(5). A copy of the sequence listing is also provided as required under 37 C.F.R. § 1.821(e), as an ASCII text file in computer readable form 4.0 kb in size created on Sep. 30, 2016, and designated H0738902.

TECHNICAL FIELD

The present invention relates to a polyamide compound, an agent for promoting replication of a mitochondrial DNA (hereinafter sometimes referred to as mtDNA) comprising the same, and a pharmaceutical composition for treating a mitochondrial genetic disease comprising the same. A mitochondrial genetic disease such as mitochondrial myopathy, encephalopathy, lactic acidosis, or stroke-like episodes can be treated or prevented by the present invention.

BACKGROUND ART

A mitochondrion is a cell organelle bearing an energy production characteristic in a eukaryotic cell, and supplies chemical energy (ATP) to a cell by an oxidative phosphorylation (OXPHOS). A mtDNA is a multicopy, circular, double-stranded DNA with 16.5 kb, and codes for 13 polypeptides, which are subunit proteins of 4 respiratory chain complexes essentially necessary for OXPHOS, 2 ribosomal RNAs (12S rRNA, and 16S rRNA) and 22 transfer RNAs (tRNAs), which are crucial for a mitochondrial protein synthesis.

Mitochondria supply 90% of energy necessary for a cell by OXPHOS in the form of ATP. Therefore, if a mitochondrial dysfunction happens, failures may ensue in central nerves, skeletal muscles, or cardiac muscles, which all have high demand for energy. In particular, a mitochondrial disease developed in central nerves or muscles is called mitochondrial myopathy, and classified into 3 disease-patterns on the basis of clinical conditions, i.e., mitochondrial myopathy, encephalopathy, lactic acidosis, and stroke-like episodes (hereinafter referred to as MELAS), myoclonic epilepsy associated with ragged-red fibers (hereinafter referred to as MERRF), and chronic, progressive, external ophthalmoplegia (hereinafter referred to as CPEO).

In the above three disease-patterns, MELAS is a lethal mitochondrial genetic disease characterized by a stroke-like episode, hyperlactacidemia or the like, which highly frequently ensues in mitochondrial diseases. Pathogenetic point mutations which cause MELAS exist intensively in a mitochondrial $tRNA^{Leu(UUR)}$ gene, and 80% of MELAS patients have a one-base substitution (hereinafter referred to as A3243G mutation) of adenine (A) to guanine (G) at mitochondrial base number 3243 on the mitochondrial $tRNA^{Leu}_{(UUR)}$ gene in mtDNAs (see FIG. 1). It is known that an A3243G mutation may cause various clinical symptoms including MELAS, such as mitochondrial diabetes, deafness, cardiomyopathy, or CPEO. In the research of molecular pathology, the A3243G mutation is a point mutation on which studies have advanced most. In the MELAS A3243G mutation mtDNAs and normal (wild) mtDNAs coexist in the same cell, and this condition is called heteroplasmy. MELAS is developed when a ratio of the A3243G mutation mtDNAs becomes in excess of 60 to 95% in a cell, which is called the threshold effect.

As a medicament for treating a mitochondrial genetic disease including MELAS, a pharmaceutical composition containing a pyrimidine nucleotide precursor and creatine as an active ingredient (Patent literature 1), a pharmaceutical composition containing 4-(p-quinolyl)-2-hydrozybutaneamide derivative as an active ingredient (Patent literature 2), a pharmaceutical composition containing alanine as an active ingredient (Patent literature 3), and so on, are known. However, the target of the known pharmaceutical compositions as above is not the gene mutations, which are the primary cause of MELAS, but the purposes thereof are merely symptomatic treatment for the conditions in central nerves or muscles. Thus, the effects thereof were limited.

As a treatment wherein a target is the gene mutation causing the mitochondrial genetic disease, a selective inhibition of replication of the MERRF mutation mtDNAs by binding peptide nucleic acids (hereinafter referred to as PNA) to an A8344G mutation which is the MERRF mutation was attempted (Non-patent literature 1). Specifically, effects on inhibition of replication of the A8344G mutation mtDNAs of MERRF in vitro by PNA in mtDNA replication run-off assay system, using PNA capable of binding to a sequence of a single-stranded H-chain existing in the MERRF A8344G mutation mtDNA under replication were assayed (Non-patent literature 1). In experiments therein, truncated mtDNAs, wherein synthesized extension was inhibited, were detected, and thus, inhibition of replication of the A8344G mutant mtDNAs by PNA was observed. However, when MERRF cybrid cells were cultured in a medium to which PNA was added, a shift of heteroplasmy to normal (wild-type) mtDNAs was not observed, namely, an effect of inhibition of replication of the A8344G mutation mtDNAs by PNA in living cells was not observed (Non-patent literature 2).

CITATION LIST

Patent Literatures

[Patent literature 1] Japanese Translation Publication (Kohyo) No. 2004-538326
[Patent literature 2] Japanese Translation Publication (Kohyo) No. 2011-503005
[Patent literature 3] WO2003/068215

Non-Patent Literatures

[Non-patent literature 1] Nature Genetics, Britain, 1997, Vol. 15, pp. 212-215.

[Non-patent literature 2] Advanced Drug Delivery Reviews, Netherlands, 2001, Vol. 49, pp. 121-125.

SUMMARY OF INVENTION

Technical Problem

As mentioned above, the conventional therapy for mitochondrial genetic disease is mainly symptomatic therapy, with no established fundamental therapy. As above, a selective inhibition of replication of MERRF mutant mtDNA using PNA is tried as treatment for diseases caused by the MERRF A8344G mutation. However, the experiment was carried out using an in vitro reconstituted system of mtDNA replication by cell fractions. Therefore, a therapeutic effect of PNA has not been confirmed in an experiment system using cells. Mitochondria have lipid bilayers. Thus, in order to deliver the PNA to the target mitochondrial A8344G mutation, it is necessary to permeate the mitochondrial lipid bilayers as well as the cell membrane. Therefore, a treatment targeting a mutation of mitochondrial genetic disease is difficult, in the light of drug delivery. In particular, a treatment targeting the A3243G mutation of MELAS patients, which is known as a fatal disease in mitochondrial genetic disease, was not tried at all.

The object of the present invention is to provide a fundamental therapy to MELAS caused by the A3243G mutation of the mtDNA, and a pharmaceutical composition used for the same. Further, the object of the present invention is to provide a fundamental therapy to a mitochondrial genetic disease caused by an A3236G mutation, mitochondrial genetic diseases caused by an A3243T mutation, a mitochondrial genetic disease caused by a G3244A mutation, a mitochondrial genetic disease caused by a G3249A mutation, mitochondrial genetic diseases caused by a T3250C mutation, a mitochondrial genetic disease caused by an A3251G mutation, a mitochondrial genetic disease caused by an A3252G mutation, a mitochondrial genetic disease caused by a C3254A mutation, a mitochondrial genetic disease caused by a C3254G mutation, a mitochondrial genetic disease caused by a G3255A mutation, mitochondrial genetic diseases caused by a C3256T mutation, mitochondrial genetic diseases caused by a T3258C mutation, or mitochondrial genetic diseases caused by an A3260G mutation, and a pharmaceutical composition used for the same.

Solution to Problem

The present inventors have conducted intensive studies into a treatment of MELAS caused by the A3243G mutation. As a result, the present inventors surprisingly found that a replication of the wild-type mtDNA is increased by a polyamide compound binding to the wild-type mtDNA sequence, to thereby shift a heteroplasmy of the wild-type mtDNA and the A3243G mutant mtDNA from the A3243G mutant mtDNA to the wild-type mtDNA, and thus, MELAS can be treated. Hitherto, it is known that polyamide compound inhibits gene expression. However, it is surprising that a polyamide compound can promote a replication of the wild-type mtDNA selectively. Further, the present inventors found that the polyamide compound of the present invention is effective for mitochondrial genetic diseases caused by the A3236G mutation, the A3243T mutation, the G3244A mutation, the G3249A mutation, the T3250C mutation, the A3251G mutation, the A3252G mutation, the C3254A mutation, the C3254G mutation, the G3255A mutation, the C3256T mutation, the T3258C mutation, or the A3260G mutation. Furthermore, the effect of the PNA in therapy cannot be confirmed in living cells. However, the effect of the pharmaceutical composition using the polyamide compound of the present invention is confirmed in living cells. Therefore, it is estimated that the polyamide compound can reach the mtDNA through a cell membrane and a mitochondrial lipid bilayers.

The present invention is based on the above findings.

Namely, the present invention relates to:

[1] a polyamide compound binding to a target double-stranded DNA, wherein said target double-stranded DNA comprises at least one nucleotide pair selected from the group consisting of an A/T pair consisting of the first A of the following sense-stranded DNA and the corresponding T, an A/T pair consisting of the 8th A of the following sense-stranded DNA and the corresponding T, a G/C pair consisting of the 9th G of the following sense-stranded DNA and the corresponding C, a G/C pair consisting of the 14th G of the following sense-stranded DNA and the corresponding C, a T/A pair consisting of the 15th T of the following sense-stranded DNA and the corresponding A, an A/T pair consisting of the 16th A of the following sense-stranded DNA and the corresponding T, an A/T pair consisting of the 17th A of the following sense-stranded DNA and the corresponding T, a C/G pair consisting of the 19th C of the following sense-stranded DNA and the corresponding G, a G/C pair consisting of the 20th G of the following sense-stranded DNA and the corresponding C, a C/G pair consisting of the 21st C of the following sense-stranded DNA and the corresponding G, a T/A pair consisting of the 23rd T of the following sense-stranded DNA and the corresponding A, an A/T pair consisting of the 25th A of the following sense-stranded DNA and the corresponding T, in the double stranded DNA of the following formula (1):

[Chem. 1]
5'-ATGGCAGAGCCCGGTAATCGCATAA-3'

3'-TACCGTCTCGGGCCATTAGCGTATT-5'          (1)

which consists of the sensestranded DNA having a base sequence of 5'-ATGGCAGAGCCCGGTAATCGCATAA-3' (SEQ ID NO: 1) and the antisense-stranded DNA having a base sequence of 5'-TTATGCGATTACCGGGCTCTGC-CAT-3' (SEQ ID NO: 2); and at least one end of said target double-stranded DNA is an A/T or T/A pair; (1) a residue of the polyamide compound, corresponding to the A/T pair or T/A pair at one end thereof is a turn structure selected from the group consisting of γ-aminobutyric acid residue, (R)2,4-diaminobutyric acid residue, and 5-aminovaleric acid residue, wherein the hydrogen atom of the residues may be substituted with an alkyl group having 1 to 4 carbon atoms, an amino group, a hydroxyl group, a carboxyl group, or —NH$_3$; (2) the binding region of the polyamide compound, corresponding to the target double-stranded DNA except for the A/T pair or T/A pair at one end thereof, is composed of
(a) Im/Py, or Im/β, corresponding to the G/C pair of the target double-stranded DNA,
(b) Py/Im, or β/Im, corresponding to the C/G pair of the target double-stranded DNA,
(c) Py/Py, Py/Hp, Py/β, β/Py, or β/β corresponding to the A/T pair of the target double-stranded DNA, and
(d) Py/Py, Hp/Py, Py/β, β/Py, or β/β, corresponding to the T/A pair of the target double-stranded DNA,
(wherein Im is N-methylimidazole, Py is N-methylpyrrole, Hp is 3-hydroxy-N-methylpyrrole, and β is β-alanine; and Im/β corresponding to the G/C pair and β/Im corresponding to the C/G pair can be only used in the case of a successive Im•β/Im•β corresponding to a successive G•C/G•C pair or a successive β•Im/β•Im corresponding to a successive C•G/C•G pair; and the hydrogen atom of the Im residue, Py residue, Hp residue, or β residue may be substituted to an alkyl group having 1 to 4 carbon atoms, an amino group, a hydroxyl group, a carboxyl group, or —NH$_3$), (3) an end of the polyamide compound corresponding to the 5'end of the other end of the target double-stranded DNA is an amino group of Im residue, an amino group of Py residue, an amino group of Hp residue, an amino group of β-alanine, a hydrogen atom, an alkyl group having 1 to 4 carbon atoms, a hydroxyl group, a carboxyl group, or an acyl group having 1 to 4 carbon atoms; an end of the polyamide compound corresponding to the 3'end of the other end of the target double-stranded DNA is a carboxyl group of Im residue, a carboxyl group of Py residue, a carboxyl group of Hp residue, a carboxyl group of β-alanine, an N,N-dimethylaminopropyl residue, or a β-alanine•N,N-dimethylaminopropyl residue,

[2] the polyamide compound of item [1], of the formula selected from the group consisting of Formula (2):
[Chem. 2]

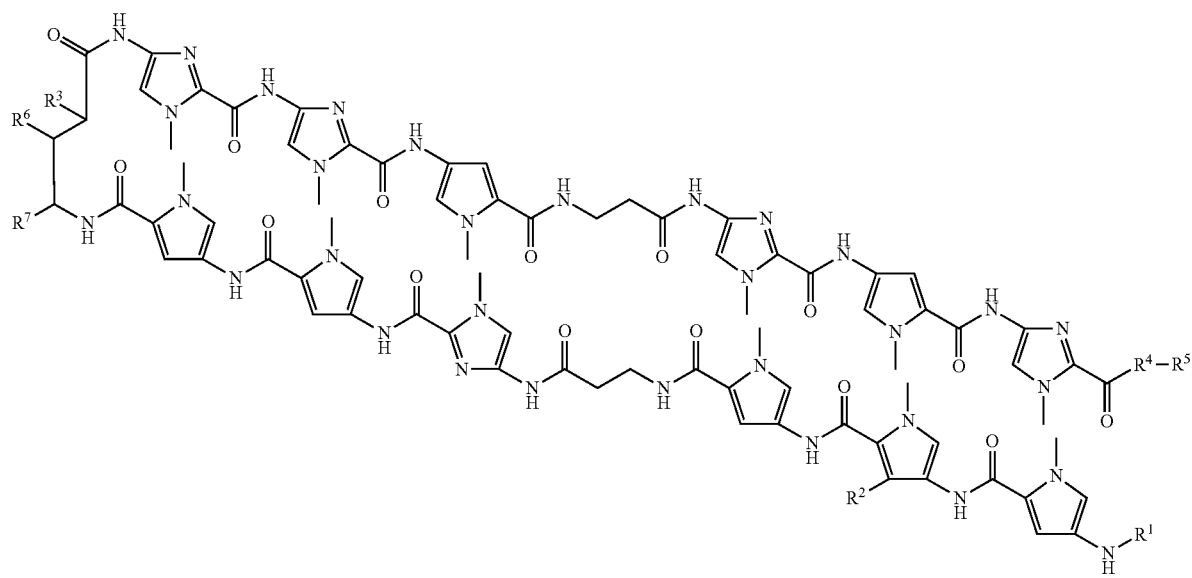

(2)

Formula (3):
[Chem. 3]

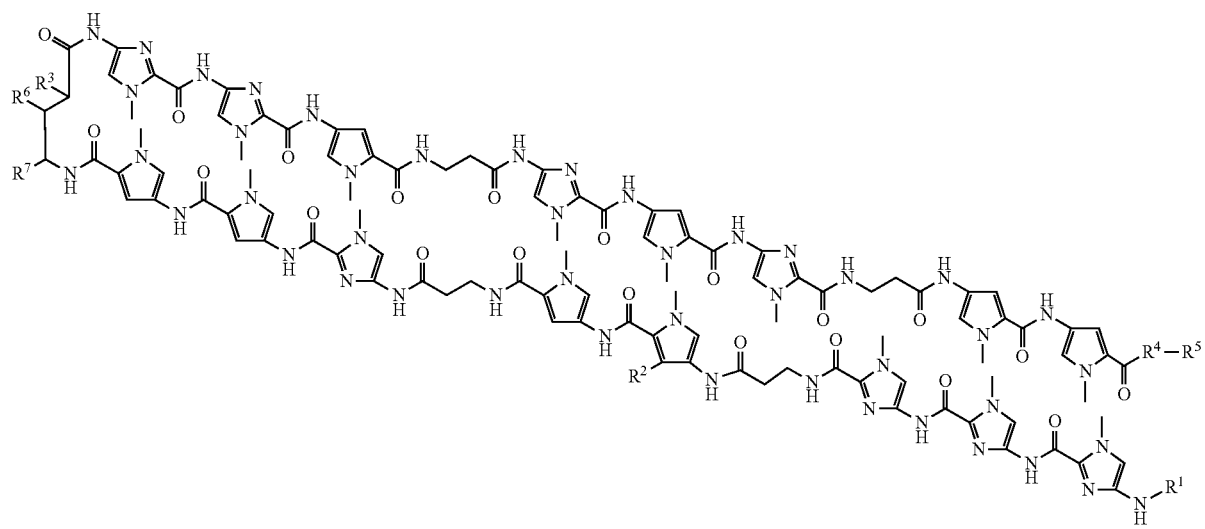

(3)

-continued
Formula (4):
[Chem. 4]
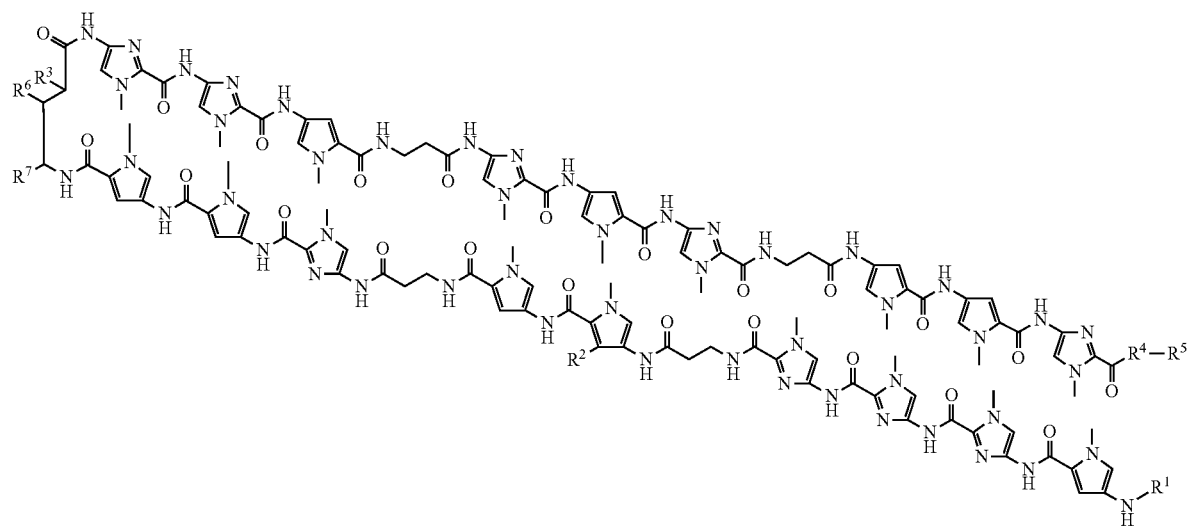
Formula (5):
[Chem. 5]
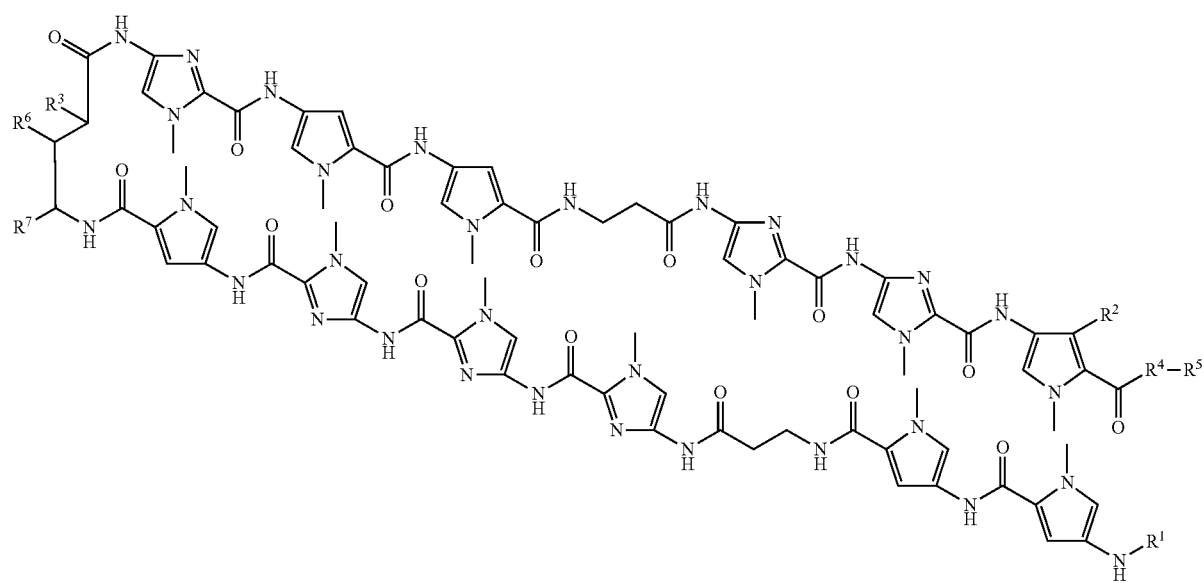

Formula (6):
[Chem. 6]
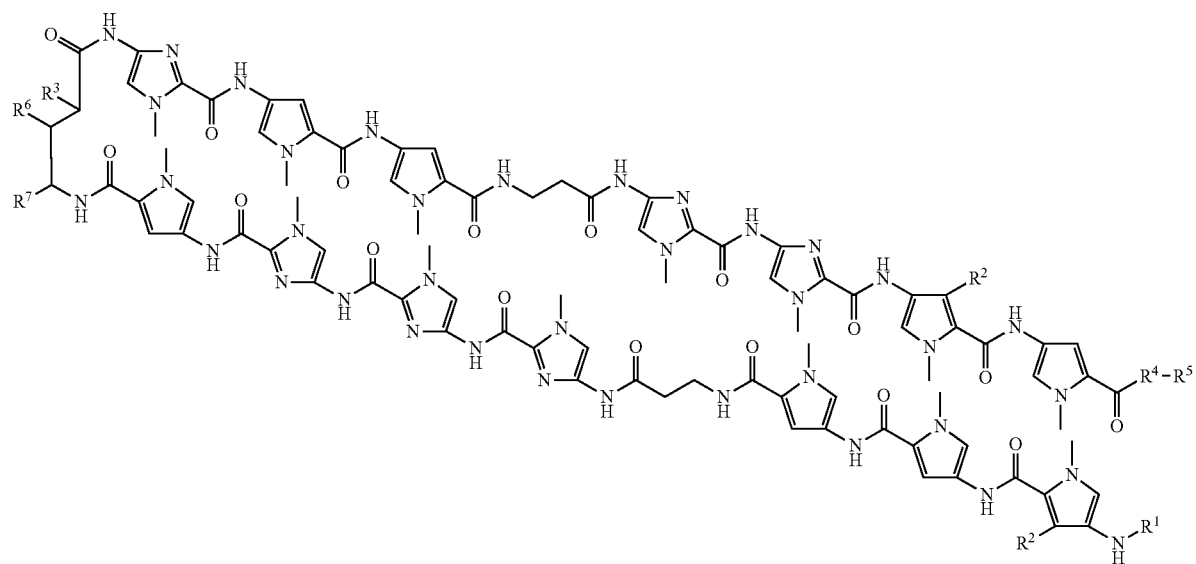
Formula (7):
[Chem. 7]
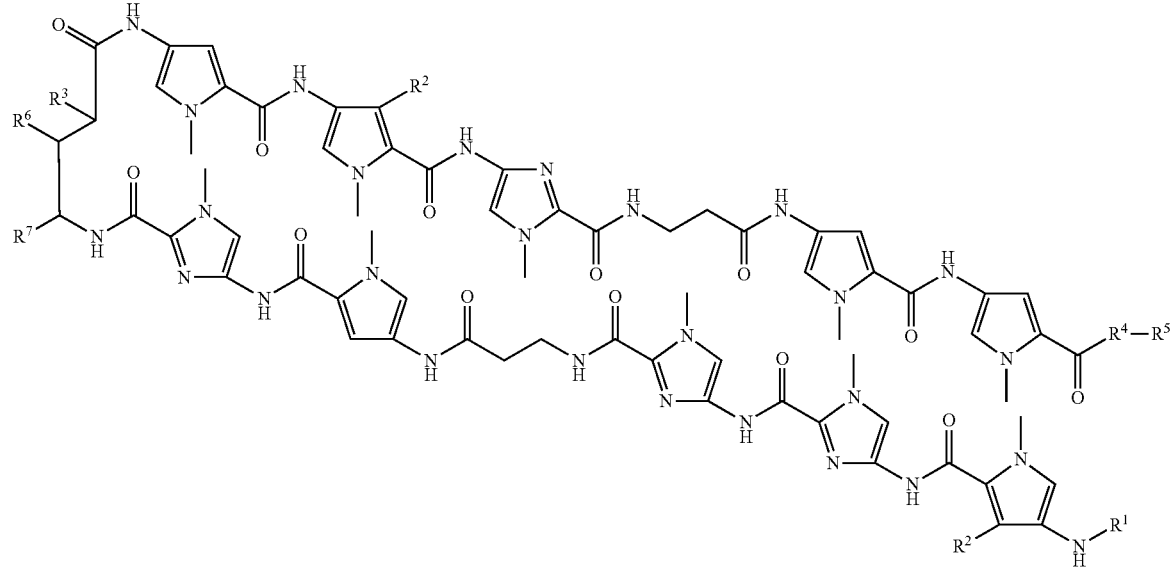

Formula (8):
[Chem. 8]
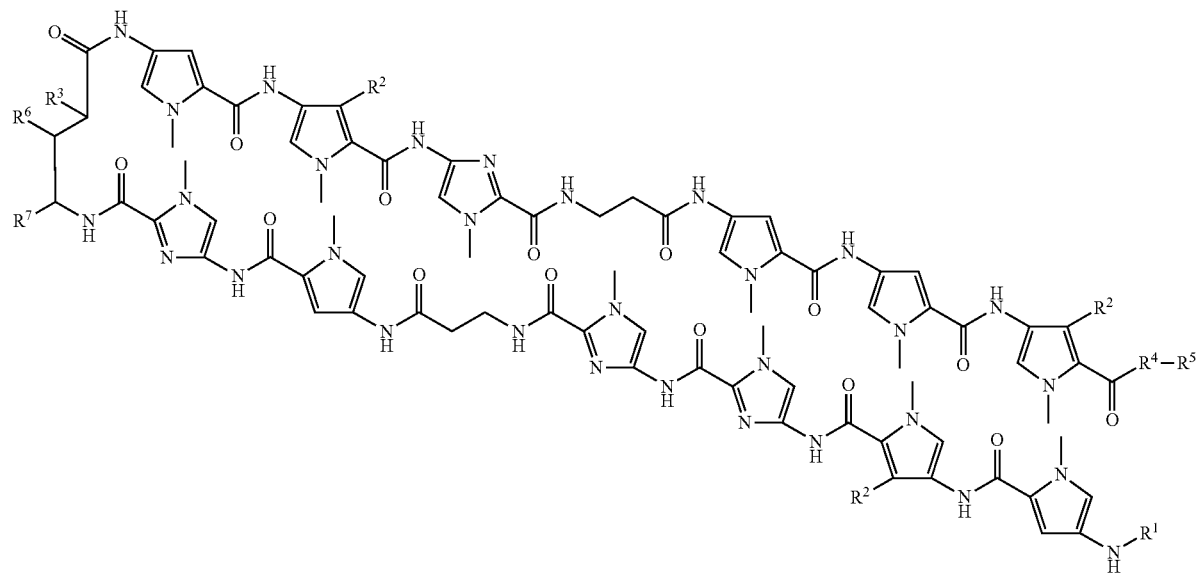
Formula (9):
[Chem. 9]
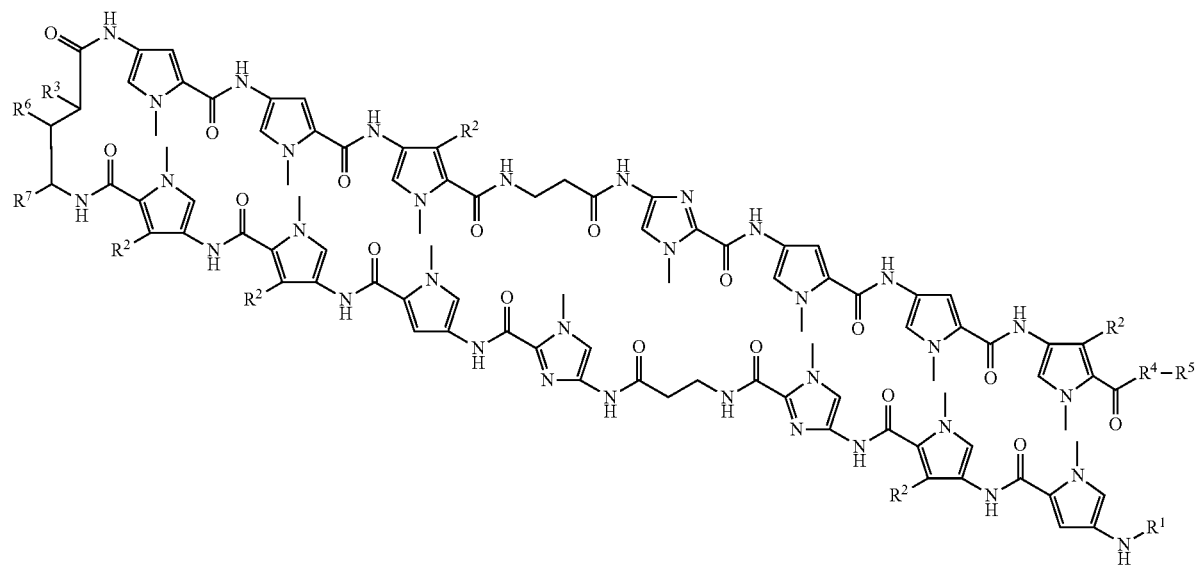

Formula (10):
[Chem. 10]

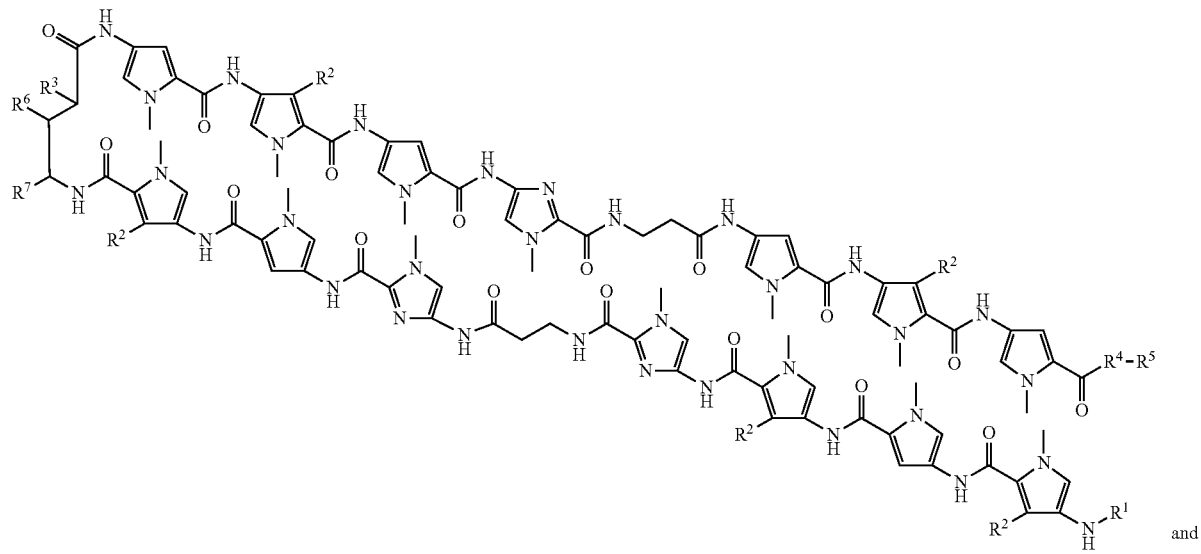

(10)

and

Formula (11):
[Chem. 11]

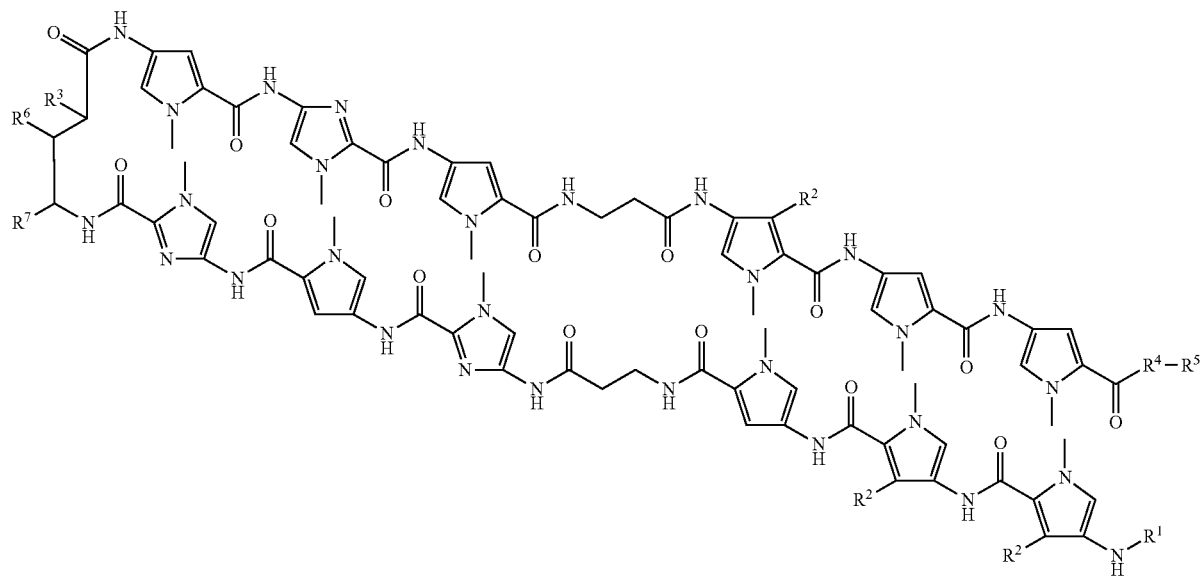

(11)

[wherein, $R^1$ is a hydrogen atom, an alkyl group having 1 to 4 carbon atoms, an hydroxyl group, an amino group, a carboxyl group, or an acyl group having 1 to 4 carbon atoms, $R^2$ is independently a hydrogen atom, or a hydroxyl group, $R^1$, $R^6$, and $R^7$ are independently a hydrogen atom, an amino group, or —$NH_3$, $R^4$ is a single bond, or β-alanine residue, $R^5$ is a hydroxyl group, or N,N-dimethylaminopropyl residue; and the hydrogen atom of the Im residue, Py residue, Hp residue, β residue, γ-aminobutyric acid residue, or (R) 2,4-diaminobutyric acid residue may be substituted with an alkyl group having 1 to 4 carbon atoms, an amino group, a hydroxyl group, or a carboxyl group],

[3] the polyamide compound of item [2], of Formula (12):

[Chem. 12]

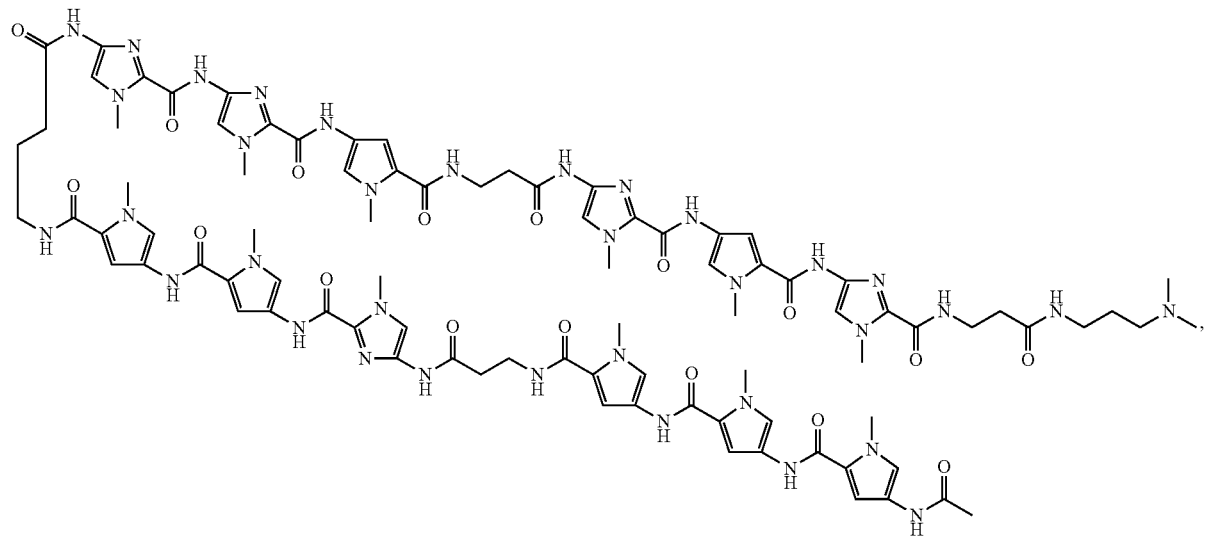

(12)

[4] an agent for promoting replication of wild-type mitochondrial DNA characterized by comprising the polyamide compound of items [1] to [3], or a pharmaceutically acceptable salt thereof, as an active ingredient,

[5] a pharmaceutical composition characterized by comprising the polyamide compound of items [1] to [3], or a pharmaceutically acceptable salt thereof, as an active ingredient,

[6] a pharmaceutical composition for treating or preventing sporadic bilateral optic neuropathy with an A3236G mutation, characterized by comprising the polyamide compound of item [1] or [2], having a residue corresponding to an A/T pair consisting of the first A of the sense-stranded DNA 5'-ATGGCAGAGCCCGGTAATCGCATAA-3' (SEQ ID NO: 1) and the corresponding T, or a pharmaceutically acceptable salt thereof, as an active ingredient,

[7] a pharmaceutical composition for treating or preventing mitochondrial myopathy, encephalopathy, lactic acidosis, stroke-like episodes; diabetes and hypacusia; mitochondrial myopathy; Leigh's syndrome; sensory deafness; chronic progressive external ophthalmoplegia; diabetes with matricliny hypacusia; or focal segmental glomerulosclerosis, with an A3243G mutation, characterized by comprising the polyamide compound of items [1] to [3], having a residue corresponding to an A/T pair consisting of the 8th A of the sense-stranded DNA 5'-ATGGCAGAGCCCGGTAATCGCATAA-3' (SEQ ID NO: 1) and the corresponding T, or a pharmaceutically acceptable salt thereof, as an active ingredient,

[8] a pharmaceutical composition for treating or preventing mitochondrial myopathy, encephalopathy, lactic acidosis, stroke-like episodes; mitochondrial myopathy; sensory deafness; or chronic progressive external ophthalmoplegia, with an A3243T mutation, characterized by comprising the polyamide compound of items [1] to [3], having a residue corresponding to an A/T pair consisting of the 8th A of the sense-stranded DNA 5'-ATGGCAGAGCCCGGTAATCGCATAA-3' (SEQ ID NO: 1) and the corresponding T, and the residue corresponding to T of the A/T pair is Hp residue, or a pharmaceutically acceptable salt thereof, as an active ingredient,

[9] A pharmaceutical composition for treating or preventing mitochondrial myopathy, encephalopathy, lactic acidosis, stroke-like episodes with a G3244A mutation, characterized by comprising the polyamide compound of items [1] to [3], having a residue corresponding to a G/C pair consisting of the 9th G of the sense-stranded DNA 5'-ATGGCAGAGCCCGGTAATCGCATAA-3' (SEQ ID NO: 1) and the corresponding C, or a pharmaceutically acceptable salt thereof, as an active ingredient,

[10] a pharmaceutical composition for treating or preventing Kearns-Sayre syndrome with a G3249A mutation, characterized by comprising the polyamide compound of item [1] or [2], having a residue corresponding to a G/C pair consisting of the 14th G of the sense-stranded DNA 5'-ATGGCAGAGCCCGGTAATCGCATAA-3' (SEQ ID NO: 1) and the corresponding C, or a pharmaceutically acceptable salt thereof, as an active ingredient,

[11] a pharmaceutical composition for treating or preventing mitochondrial myopathy, or chronic progressive external ophthalmoplegia with a T3250C mutation, characterized by comprising the polyamide compound of item [1] or [2], having a residue corresponding to a T/A pair consisting of the 15th T of the sense-stranded DNA 5'-ATGGCAGAGCCCGGTAATCGCATAA-3' (SEQ ID NO: 1) and the corresponding A, or a pharmaceutically acceptable salt thereof, as an active ingredient,

[12] a pharmaceutical composition for treating or preventing mitochondrial myopathy with an A3251G mutation, characterized by comprising the polyamide compound of item [1] or [2], having a residue corresponding to a A/T pair consisting of the 16th A of the sense-stranded DNA 5'-ATGGCAGAGCCCGGTAATCGCATAA-3' (SEQ ID NO: 1) and the corresponding T, or a pharmaceutically acceptable salt thereof, as an active ingredient,

[13] a pharmaceutical composition for treating or preventing mitochondrial myopathy, encephalopathy, lactic acidosis, stroke-like episodes with an A3252G mutation, characterized by comprising the polyamide compound of item [1] or [2], having a residue corresponding to a A/T pair consisting of the 17th A of the sense-stranded DNA 5'-ATGGCAGAGCCCGGTAATCGCATAA-3' (SEQ ID NO: 1) and the corresponding T, or a pharmaceutically acceptable salt thereof, as an active ingredient,

[14] a pharmaceutical composition for treating or preventing diabetes in pregnancy with a C3254A mutation, or mitochondrial myopathy with a C3254G mutation, characterized by comprising the polyamide compound of item [1] or [2], having a residue corresponding to a C/G pair consisting of the 19th C of the sense-stranded DNA 5'-ATGGCAGAGCCCGGTAATCGCATAA-3' (SEQ ID NO: 1) and the corresponding G, or a pharmaceutically acceptable salt thereof, as an active ingredient,

[15] a pharmaceutical composition for treating or preventing MERRF/KSS overlap syndrome with a G3255A mutation, characterized by comprising the polyamide compound of item [1] or [2], having a residue corresponding to a G/C pair consisting of the 20th G of the sense-stranded DNA 5'-ATGGCAGAGCCCGGTAATCGCATAA-3' (SEQ ID NO: 1) and the corresponding C, or a pharmaceutically acceptable salt thereof, as an active ingredient,

[16] a pharmaceutical composition for treating or preventing mitochondrial myopathy, encephalopathy, lactic acidosis, stroke-like episodes/myoclonic epilepsy with ragged-red fibers with a C3256T mutation, characterized by comprising the polyamide compound of item [1] or [2], having a residue corresponding to a C/G pair consisting of the 21st C of the sense-stranded DNA 5'-ATGGCAGAGCCCGGTAATCGCATAA-3' (SEQ ID NO: 1) and the corresponding G, or a pharmaceutically acceptable salt thereof, as an active ingredient,

[17] a pharmaceutical composition for treating or preventing mitochondrial myopathy, encephalopathy, lactic acidosis, stroke-like episodes/myopathy with a T3258C mutation, characterized by comprising the polyamide compound of item [1] or [2], having a residue corresponding to a T/A pair consisting of the 23rd T of the sense-stranded DNA 5'-ATGGCAGAGCCCGGTAATCGCATAA-3' (SEQ ID NO: 1) and the corresponding A, or a pharmaceutically acceptable salt thereof, as an active ingredient,

[18] a pharmaceutical composition for treating or preventing adult matricliny myopathy and cardiac myopathy with an A3260G mutation, characterized by comprising the polyamide compound according to claim 1 or 2, having a residue corresponding to a A/T pair consisting of the 25th A of the sense-stranded DNA 5'-ATGGCAGAGCCCGGTAATCGCATAA-3' (SEQ ID NO: 1) and the corresponding T, or a pharmaceutically acceptable salt thereof, as an active ingredient.

Advantageous Effects of Invention

According to the polyamide compound of the present invention, the replication of the wild-type mtDNA can be selectively promoted, and further, the pharmaceutical composition for treating mitochondrial genetic disease can be prepared. Furthermore, according to the pharmaceutical composition of the present invention, the mitochondrial genetic disease was caused by at least one mutation selected from the group consisting of the A3236G mutation, the A3243G mutation, the A3243T mutation, the G3244A mutation, the G3249A mutation, the T3250C mutation, the A3251G mutation, the A3252G mutation, the C3254A mutation, the C3254G mutation, the G3255A mutation, the C3256T mutation, the T3258C mutation, and the A3260G mutation.

In the treatment using the PNA by inhibiting the replication of mutant mtDNA, it is necessary to prepare one PNA against one mutation. However, in the treatment using the pharmaceutical composition comprising the polyamide compound of the present invention, the wild-type mtDNA is targeted. Therefore, a mitochondrial genetic disease caused by multiple mtDNA mutations can be treated using one polyamide compound. In addition, in the treatment using the PNA by inhibiting the replication of mutant mtDNA, the object of the treatment is to decrease the mutant mtDNA, and therefore the wild-type mtDNA cannot increase directly. Thus, an energy production decreased by mitochondrial genetic disease cannot be recovered in cells. However, in the treatment of the pharmaceutical composition of the present invention, the wild-type mtDNA can increase, and thus a cause of mitochondrial genetic disease can be fundamentally improved.

BRIEF DESCRIPTION OF THE DRAWINGS

FIG. 2 is a schematic view showing a wild-type double-stranded DNA sequence to which the polyamide compound of the present invention binds, and the polyamide compounds of embodiment a1, embodiment a2, embodiment a3, embodiment b1, embodiment b2, embodiment c1, embodiment c2, embodiment c3, embodiment d1, embodiment e1, and embodiment f1. The dot (•) in the view means a base in which mutations in mitochondrial genetic disease may be presented.

FIG. 7 is a photograph showing morphologies of 143B cells treated with 1 μM of ML1 polyamide (4A), 143B cells treated with 500 nM or 100 nM of ML1 polyamide (4B), and HeLa cells treated with 1 μM of ML1 polyamide (4C), for

DESCRIPTION OF EMBODIMENTS

[1] Polyamide Compound

Figure 1:
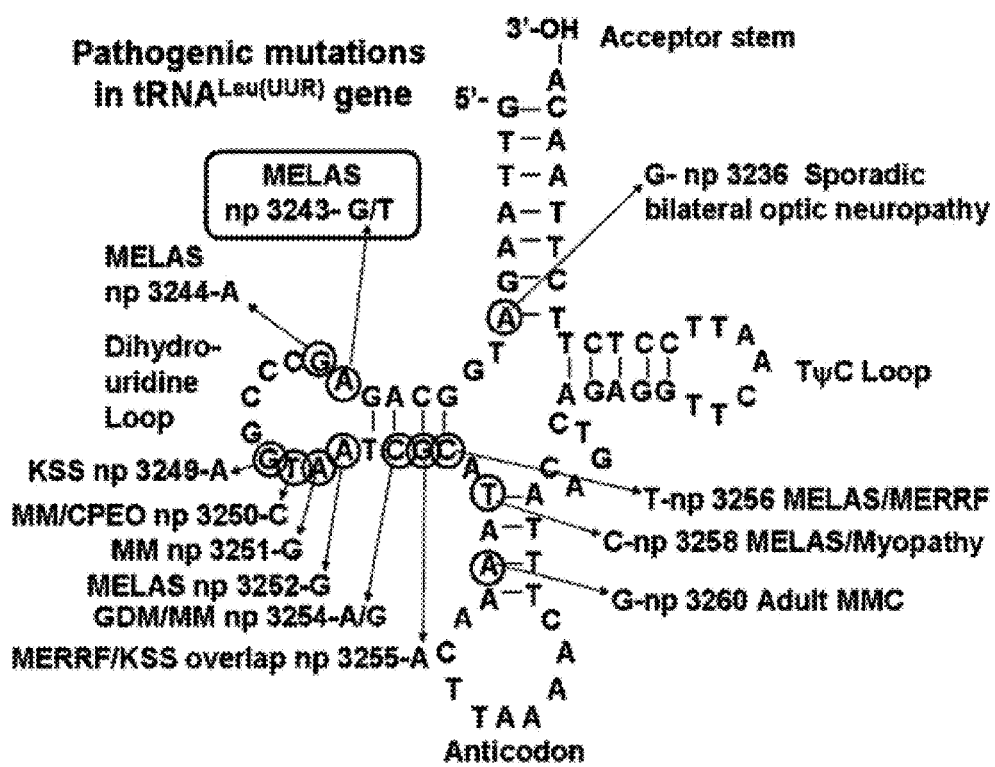
FIG. 1 is a view showing disease-causing point mutations on a mitochondrial tRNA$^{Leu(UUR)}$ gene.

The polyamide compound of the present invention comprises at least one nucleotide pair selected from the group consisting of an A/T pair consisting of the first A of the following sense-stranded DNA and the corresponding T, an A/T pair consisting of the 8th A of the following sense-stranded DNA and the corresponding T, a G/C pair consisting of the 9th G of the following sense-stranded DNA and the corresponding C, a G/C pair consisting of the 14th G of the sense-stranded DNA and the corresponding C, a T/A pair consisting of the 15th T of the following sense-stranded DNA and the corresponding A, an A/T pair consisting of the 16th A of the following sense-stranded DNA and the corresponding T, an A/T pair consisting of the 17th A of the following sense-stranded DNA and the corresponding T, a C/G pair consisting of the 19th C of the following sense-stranded DNA and the corresponding G, a G/C pair consisting of the 20th G of the following sense-stranded DNA and the corresponding C, a C/G pair consisting of the 21st C of the following sense-stranded DNA and the corresponding G, a T/A pair consisting of the 23rd T of the following sense-stranded DNA and the corresponding A, an A/T pair consisting of the 25th A of the following sense-stranded DNA and the corresponding T, in the double stranded DNA of the following formula (1):

[Chem. 13]

5'-ATGGCAGAGCCCGGTAATCGCATAA-3'

3'-TACCGTCTCGGGCCATTAGCGTATT-5'     (1)

which consists of the sense-stranded DNA having a base sequences of 5'-ATGGCAGAGCCCGGTAATCGCATAA-3' (SEQ ID NO: 1) and the antisense-stranded DNA having a base sequences of 5'-TTATGCGATTACCGGGCTCTGC-CAT-3' (SEQ ID NO: 2); and at least one end of the target double-stranded DNA is an A/T or T/A pair. Further, the polyamide compound of the present invention binds to the target double-stranded DNA.

(Double-Stranded DNA)

The double-stranded DNA of the above formula (1) corresponds to the base sequence of 3236th to 3260th in mitochondria DNA, and is present in the mitochondria tRNA$^{Leu(UUR)}$ gene. In the present specification, a single-strand DNA of 5'-ATGGCAGAGCCCGGTAATCG-CATAA-3' (SEQ ID NO: 1) in double-stranded DNA is referred to as a sense-stranded DNA, and a single-strand DNA of 5'-TTATGCGATTACCGGGCTCTGCCAT-3' (SEQ ID NO: 2) in double-stranded DNA is referred to as an antisense-stranded DNA.

Mutations of mitochondrial genetic disease occur in the region of the above double-stranded DNA. As the mutation causing mitochondrial genetic disease, there may be mentioned one point mutation from adenine (A) to guanine (G) on 3236th base sequence in mitochondria DNA, i.e. the A3236G mutation, one point mutation from adenine (A) to guanine (G) on 3243th base sequence in mitochondria DNA, i.e. the A3243G mutation, one point mutation from adenine (A) to thymine (T) on 3243th base sequence in mitochondria DNA, i.e. the A3243T mutation, one point mutation from guanine (G) to adenine (A) on 3244th base sequence in mitochondria DNA, i.e. the G3244A mutation, one point mutation from guanine (G) to adenine (A) on 3249th base sequence in mitochondria DNA, i.e. the G3249A mutation, one point mutation from thymine (T) to cytosine (C) on 3250th base sequence in mitochondria DNA, i.e. the T3250C mutation, one point mutation from adenine (A) to guanine (G) on 3251th base sequence in mitochondria DNA, i.e. the A3251G mutation, one point mutation from adenine (A) to guanine (G) on 3252th base sequence in mitochondria DNA, i.e. the A3252G mutation, one point mutation from cytosine (C) to adenine (A) on 3254th base sequence in mitochondria DNA, i.e. the C3254A mutation, one point mutation from cytosine (C) to guanine (G) on 3254th base sequence in mitochondria DNA, i.e. the C3254G mutation, one point mutation from guanine (G) to adenine (A) on 3255th base sequence in mitochondria DNA, i.e. the G3255A mutation, one point mutation from cytosine (C) to thymine (T) on 3256th base sequence in mitochondria DNA, i.e. the C3256T mutation, one point mutation from thymine (T) to cytosine (C) on 3258th base sequence in mitochondria DNA, i.e. the T3258C mutation, one point mutation from adenine (A) to guanine (G) on 3260th base sequence in mitochondria DNA, i.e. the A3260G mutation.

(Target Double-Stranded DNA)

In the above double-stranded DNA, target double-stranded DNA wherein the polyamide compound of the present invention binds, are included. The target double-stranded DNA contains at least one nucleotide pair of wild-type mtDNA corresponding to the A3236G mutation, the A3243G mutation, the A3243T mutation, the G3244A mutation, the G3249A mutation, the T3250C mutation, the A3251G mutation, the A3252G mutation, the C3254A mutation, the C3254G mutation, the G3255A mutation, the C3256T mutation, the T3258C mutation, or the A3260G mutation. Specifically, the target double-stranded DNA contains at least one nucleotide pair selected from the group consisting of an A/T pair consisting of the first A of the sense-stranded DNA and the corresponding T, an A/T pair consisting of the 8th A of the sense-stranded DNA and the corresponding T, a G/C pair consisting of the 9th G of the sense-stranded DNA and the corresponding C, a G/C pair consisting of the 14th G of the sense-stranded DNA and the corresponding C, a T/A pair consisting of the 15th T of the sense-stranded DNA and the corresponding A, an A/T pair consisting of the 16th A of the sense-stranded DNA and the corresponding T, an A/T pair consisting of the 17th A of the sense-stranded DNA and the corresponding T, a C/G pair consisting of the 19th C of the sense-stranded DNA and the corresponding G, a G/C pair consisting of the 20th G of the sense-stranded DNA and the corresponding C, a C/G pair consisting of the 21st C of the sense-stranded DNA and the corresponding G, a T/A pair consisting of the 23rd T of the sense-stranded DNA and the corresponding A, an A/T pair consisting of the 25th A of the sense-stranded DNA and the corresponding T. The polyamide compound of the present invention can preferentially bind to the wild-type mtDNA, but cannot bind to mutant mtDNA or can scarcely bind to mutant mtDNA.

The target double-stranded DNA contains a T/A or A/T pair at one end thereof. The T/A or A/T pair corresponds to a turn structure of the polyamide compound. On the other hand, a nucleotide pair of the other end of the target double-stranded DNA has no particular limitation, and may be a T/A pair, an A/T pair, a G/C pair, or a C/G pair.

As a T/A pair or A/T pair on the one end, there may be mentioned an A/T pair consisting of the first A of sense-stranded DNA in the double-stranded DNA of the following formula (1):

```
[Chem. 14]
5'-ATGGCAGAGCCCGGTAATCGCATAA-3'

3'-TACCGTCTCGGGCCATTAGCGTATT-5'        (1)
``` and the corresponding T. The target double-stranded DNA containing the above A/T pair has a length of 8 bp to 16 bp.

As another T/A pair or A/T pair on the one end, there may be mentioned a T/A pair consisting of the second T of sense-stranded DNA in the double-stranded DNA of the above formula (1) and the corresponding A. The target double-stranded DNA containing the above T/A pair has a length of 7 bp to 16 bp. For example, the target double-stranded DNA includes one having a length of 8 bp of the following formula (13):

```
[Chem. 15]
5'-TGGCAGAG-3'

3'-ACCGTCTC-5',                        (13)
```

SEQ ID NOs: 3 and 13
one having a length of 11 bp of the following formula (14):

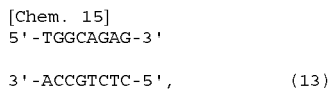

SEQ ID NOs: 4 and 14
one having a length of 12 bp of the following formula (15):

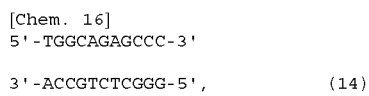

SEQ ID NOs: 5 and 15.

As another T/A pair or A/T pair on the one end, there may be mentioned an A/T pair consisting of the sixth A of sense-stranded DNA in the double-stranded DNA of the above formula (1) and the corresponding T. The target double-stranded DNA containing the above A/T pair has a length of 3 bp to 16 bp.

As another T/A pair or A/T pair on the one end, there may be mentioned an A/T pair consisting of the eighth A of sense-stranded DNA in the double-stranded DNA of the above formula (1) and the corresponding T. The target double-stranded DNA containing the above A/T pair has a length of 3 bp to 16 bp. For example, the target double-stranded DNA includes one having a length of 8 bp of the following formula (16):

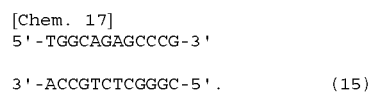

SEQ ID NOs. 6 and 16
or, one having a length of 9 bp of the following formula (17):

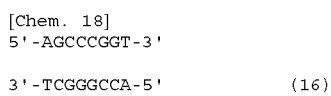

SEQ ID NOs. 7 and 17.

As another T/A pair or A/T pair on the one end, there may be mentioned a T/A pair consisting of the tenth T of antisense-stranded DNA in the double-stranded DNA of the above formula (1) and the corresponding A. The target double-stranded DNA containing the above T/A pair has a length of 3 bp to 16 bp.

As another T/A pair or A/T pair on the one end, there may be mentioned an A/T pair consisting of the eleventh A of antisense-stranded DNA in the double-stranded DNA of the above formula (1) and the corresponding T. The target double-stranded DNA containing the above A/T pair has a length of 3 bp to 15 bp.

As another T/A pair or A/T pair on the one end, there may be mentioned a T/A pair consisting of the eighteenth T of antisense-stranded DNA in the double-stranded DNA of the above formula (1) and the corresponding A. The target double-stranded DNA containing the above T/A pair has a length of 3 bp to 8 bp. For example, the target double-stranded DNA includes one having a length of 7 bp of the following formula (18):

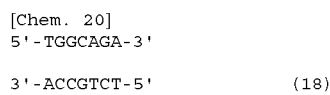

SEQ ID NOs: 8 and 18
or, one having a length of 8 bp of the following formula (19):

```
[Chem. 21]
5'-ATGGCAGA-3'

3'-TACCGTCT-5'.                        (19)
```

SEQ ID NOs: 9 and 19.

As another T/A pair or A/T pair on the one end, there may be mentioned a T/A pair consisting of the fifteenth T of sense-stranded DNA in the double-stranded DNA of the above formula (1) and the corresponding A. The target double-stranded DNA containing the above T/A pair has a length of 3 bp to 12 bp. For example, the target double-stranded DNA includes one having a length of 9 bp of the following formula (20):

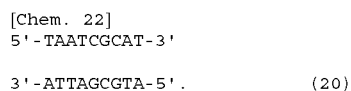

SEQ ID NOs: 10 and 20.

As another T/A pair or A/T pair on the one end, there may be mentioned an A/T pair consisting of the sixteenth A of sense-stranded DNA in the double-stranded DNA of the above formula (1) and the corresponding T. The target double-stranded DNA containing the above A/T pair has a length of 3 bp to 110 bp. For example, the target double-stranded DNA includes one having a length of 8 bp of the following formula (21):

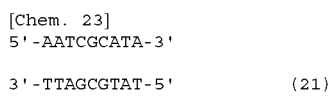

SEQ ID NOs: 11 and 21.

As another T/A pair or A/T pair on the one end, there may be mentioned an A/T pair consisting of the seventeenth A of sense-stranded DNA in the double-stranded DNA of the above formula (1) and the corresponding T. The target double-stranded DNA containing the above A/T pair has a length of 3 bp to 10 bp.

As another T/A pair or A/T pair on the one end, there may be mentioned a T/A pair consisting of the eighteenth T of sense-stranded DNA in the double-stranded DNA of the above formula (1) and the corresponding A. The target double-stranded DNA containing the above T/A pair has a length of 3 bp to 8 bp. For example, the target double-stranded DNA includes one having a length of 8 bp of the following formula (22):

[Chem. 24]
5'-TCGCATAA-3'

3'-AGCGTATT-5'        (22)

SEQ ID NOs: 12 and 22.

As another T/A or A/T pair on the one end, there may be mentioned a T/A pair consisting of the first T of antisense-stranded DNA and the corresponding A, a T/A pair consisting of the second T of the antisense-stranded DNA and the corresponding A, an A/T pair consisting of the third A of the antisense-stranded DNA and the corresponding T, a T/A pair consisting of the fourth T of the antisense-stranded DNA and the corresponding A, an A/T pair consisting of the eighth A of the antisense-stranded DNA and the corresponding T and a T/A pair consisting of the ninth T of the antisense-stranded DNA and the corresponding A in the double-stranded DNA of the above formula (1). The target double-stranded DNA containing the above T/A or A/T pair has a length of 3 bp to 16 bp.

A length of the target double-stranded DNA does not have any particular limitation, but the lower limit of the length is preferably 3 bp or more, more preferably 5 bp or more, most preferably 7 bp or more. When the length of the target double-stranded DNA is less than 3 bp, the wild-type mtDNA replication may not be improved, due to a weak binding of the polyamide compound of the present invention. The upper limit of the length is preferably 16 bp or less, more preferably 14 bp or less, most preferably 12 bp or less. When the length of the target double-stranded DNA is more than 16 bp, a flexibility of the polyamide compound may be lacking. Thus, the binding of the polyamide compound to a minor groove of B-form DNA may become poor.

(Binding Region of Polyamide Compound to Target Double-Stranded DNA)

The binding region of the polyamide compound to the target double-stranded DNA is composed of aromatic amino acid residue. The binding region of the polyamide compound can bind to the target double-stranded DNA.

The N-methylpyrrole residue (hereinafter sometimes referred to as a Py residue) used in the polyamide compound can selectively bind to thymine (T), adenine (A), and cytosine (C). Further, the N-methylimidazole residue (hereinafter sometimes referred to as an Im residue) can selectively bind to guanine (G). The 3-hydroxy-N-methylpyrrole residue (hereinafter sometimes referred to as an Hp residue) can bind to thymine (T). Further, the β-alanine residue (hereinafter sometimes referred to as a β residue) can bind to thymine (T), adenine (A), and cytosine (C). The β residue has flexibility, and therefore an orientation structure of the polyamide compound can fit a curvature of B-form DNA.

When the number of residues of polyamide compound is 5 or less, the pitch of the polyamide compound nearly fits that of the helix of B-form DNA. Thus, the polyamide compound can bind to the minor groove of B-form DNA. However, when the number of residues of polyamide compound is more than 5, it may sometimes be difficult to bind to the B-form DNA. In this case, the orientation structure of the polyamide compound can fit the curvature of B-form DNA by inserting flexible β residue into the polyamide compound.

Therefore, an Im/Py or Im/β corresponds to the G/C pair of the target double-stranded DNA. Further, Py/Im, or β/Im corresponds to the C/G pair of the target double-stranded DNA. However, Im/β corresponding to a G/C pair and β/Im corresponding to a C/G pair can only be used in the case of a successive Im•β/Im•β corresponding to a successive G•C/G•C pair or a successive Im•β/Im•β corresponding to a successive C•G/C•G pair. That is to say, when the guanine (G) and cytosine (C) are sequenced in the target double-stranded DNA, two β residues can be used simultaneously, as aromatic amino acid residues corresponding to two cytosines (C) located in a crossed position. This allows the polyamide compound to give flexibility. Therefore, it is not preferable that one β residue is used as an aromatic amino acid residue corresponding to one cytosine (C) in a GC/GC pair or a CG/CG pair, and one Py residue is used as an aromatic amino acid residue corresponding to the other cytosine (C) in a GC/GC pair or a CG/CG pair. Further, it is not preferable that one or two β residue(s) are used as aromatic amino acid residue(s) corresponding to one or two cytosine(s) in a GG/CC pair or a CC/GG pair.

A Py/Py, Py/Hp, Py/β, β/Py, or β/β corresponds to the A/T pair of the target double-stranded DNA. Further, γ-aminobutyric acid residue, (R) 2,4-diaminobutyric acid residue, or 5-aminovaleric acid residue can correspond to the A/T pair of one end of the target double-stranded DNA. However, when the γ-aminobutyric acid residue, (R) 2,4-diaminobutyric acid residue, or 5-aminovaleric acid residue corresponding to an A/T pair of one end of the target double-stranded DNA is used, the γ-aminobutyric acid residue, (R) 2,4-diaminobutyric acid residue, or 5-aminovaleric acid residue cannot be used to correspond to the A/T pair or T/A pair of the other end thereof.

A Py/Py, Hp/Py, Py/β, β/Py, β/β corresponds to the T/A pair of the target double-stranded DNA. Further, γ-aminobutyric acid residue, (R) 2,4-diaminobutyric acid residue, or 5-aminovaleric acid residue can correspond to the T/A pair of one end of the target double-stranded DNA. However, when the γ-aminobutyric acid residue, (R) 2,4-diaminobutyric acid residue, or 5-aminovaleric acid residue corresponding to the T/A pair of one end of the target double-stranded DNA is used, the γ-aminobutyric acid residue, (R) 2,4-diaminobutyric acid residue, or 5-aminovaleric acid residue cannot be used to correspond to an A/T or T/A pair of the other end thereof.

The term "N-methylpyrrole residue" as used herein means a residue of formula (23):

[Chem. 25]

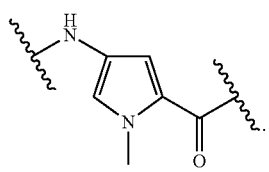

(23)

The term "N-methylimidazole residue" as used herein means a residue of formula (24):

[Chem. 26]

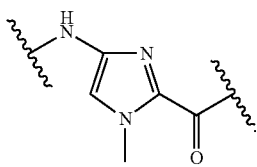
(24)

The term "3-hydroxy-N-methylpyrrole residue" as used herein means a residue of formula (25):

[Chem.27]

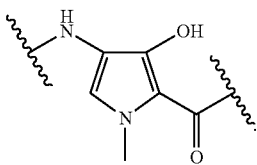
(25)

The term "β-alanine residue" as used herein means a residue of formula (26):

[Chem. 28]

(26)

The term "γ-aminobutyric acid residue" as used herein means a residue of formula (27):

[Chem. 29]

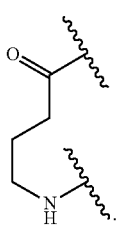
(27)

The term "(R) 2,4-diaminobutyric acid residue" as used herein means a residue of formula (28):

[Chem. 30]

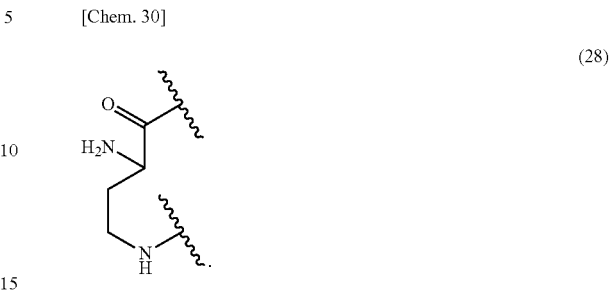
(28)

The term "5-aminovaleric acid residue" as used herein means a residue of formula (29):

[Chem. 31]

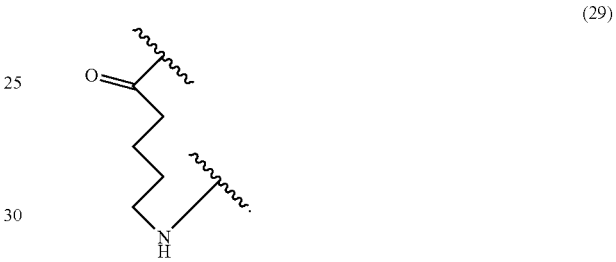
(29)

In the polyamide compound of the present invention, a hydrogen atom of Im residue, Py residue, Hp residue, β residue, may be substituted to an alkyl group having 1 to 4 carbon atoms, an amino group, a hydroxyl group, or a carboxyl group. However, a hydrogen atom is preferable. Further, a hydrogen atom of γ-aminobutyric acid residue, (R) 2,4-diaminobutyric acid residue, or 5-aminovaleric acid residue may be substituted to an alkyl group having 1 to 4 carbon atoms, an amino group, a hydroxyl group, a carboxyl group, or —$NH_3$. However, a hydrogen atom or —$NH_3$ is preferable.

(Turn Structure)

As mentioned above, at least one end of the target double-stranded DNA is an A/T or T/A pair. The residue of the polyamide compound corresponding to the above nucleotide pair is selected from the group consisting of γ-aminobutyric acid residue, (R) 2,4-diaminobutyric acid residue, and 5-aminovaleric acid residue, and these residues form a hairpin structure of the polyamide compound. In other words, the polyamide compound of the present invention is folded by the γ-aminobutyric acid residue, (R) 2,4-diaminobutyric acid residue, or 5-aminovaleric acid residue, and has a hairpin structure as a whole thereof. By the hairpin structure, each residue of a polyamide compound can correspond and bind to each base of double-stranded DNA.

(Terminal Structures of Polyamide Compound)

As mentioned above, the other end of the target double-stranded DNA is not particularly limited, and may be a T/A pair, A/T pair, G/C pair, or C/G pair. Therefore, the terminal structures of the polyamide compound may be residues corresponding to such nucleotide pairs, i.e. Im residue, Py residue, Hp residue, or β residue. That is, the terminal group of the polyamide compound may be an amino group or a carboxyl group of Im residue, Py residue, Hp residue, or β residue. Further, the terminal of the polyamide compound may have other residue, so long as the residue inhibits the binding of the polyamide compound to target double-stranded DNA.

In particular, an end of the polyamide compound corresponding to a 5' end of the other end of the target double-stranded DNA is not particularly limited, but is an amino group of Im residue, an amino group of Py residue, an amino group of Hp residue, an amino group of β-alanine, an alkyl group having 1 to 4 carbon atoms, a hydroxyl group, an amino group, a carboxyl group, or an acyl group having 1 to 4 carbon atoms; preferably an acyl group having 1 to 4 carbon atoms, more preferably an acetyl group of the following formula (30):

[Chem. 32]

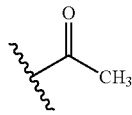
(30)

Further, an end of the polyamide compound corresponding to a 3' end of the other end of target double-stranded DNA is a carboxyl group of Im residue, a carboxyl group of Py residue, a carboxyl group of Hp residue, a carboxyl group of β-alanine, an N,N-dimethylaminopropyl residue, or a β-alanine-N,N-dimethylaminopropyl residue; preferably a β-alanine-N,N-dimethylaminopropyl residue of the following formula (31):

[Chem. 33]

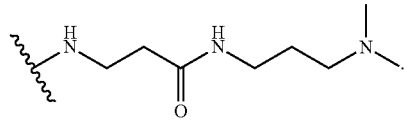
(31)

The mitochondria membrane is negatively charged (−150∼−180 mV). Thus, when the polyamide compound contains N,N-dimethylaminopropyl residue having positive charge, the polyamide compound can be actively incorporated into a mitochondrial matrix. In addition, when the polyamide compound contains β-alanine residue, flexibility between the N,N-dimethylaminopropyl residue and the binding region against target double-stranded DNA of the polyamide compound, is obtained. Therefore, it is advantageous to the binding of the polyamide compound and target double-stranded DNA.

As one embodiment of the polyamide compound which targets at the target double-stranded DNA of the above formula (13), there may be mentioned a polyamide compound (hereinafter sometimes referred to as an embodiment A1) of the following formula (2):

[Chem. 34]

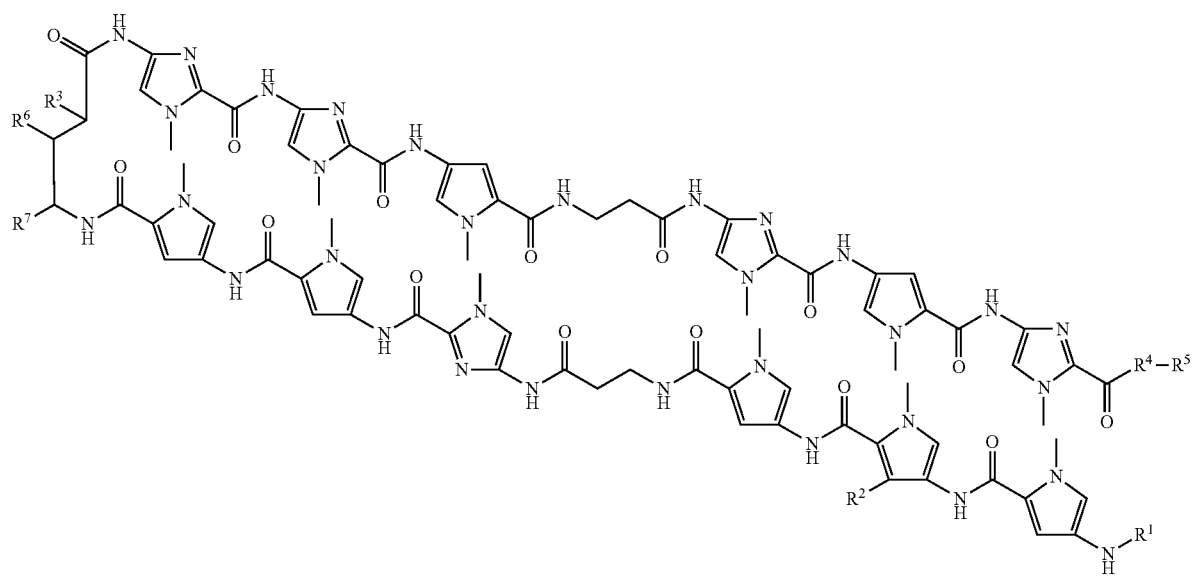
(2)

[wherein, $R^1$ is a hydrogen atom, an alkyl group having 1 to 4 carbon atoms, a hydroxyl group, an amino group, a carboxyl group, or an acyl group having 1 to 4 carbon atoms, $R^2$ is independently a hydrogen atom, or a hydroxyl group, $R^1$, $R^6$, and $R^7$ are independently a hydrogen atom, an amino groups, or —$NH_3$, $R^4$ is a single bond or β-alanine residue, $R^5$ is a hydroxyl group, or N-dimethylaminopropyl residue, and the hydrogen atom of the Im residue, Py residue, Hp residue, β residue, γ-aminobutyric acid residue, or (R) 2,4-diaminobutyric acid residue may be substituted with an alkyl group having 1 to 4 carbon atoms, an amino group, a hydroxyl group, or a carboxyl group]. As a further preferable embodiment A1, there may be mentioned Ac-Py-Py-Py-β-Im-Py-Py-γ-Im-Im-Py-β-Im-Py-Im-β-Dp (wherein, γ is γ-aminobutyric acid residue, Dp is N,N-dimethylaminopropyl residue, and the "residue" is conveniently abbreviated; hereinafter sometimes referred to as an embodiment a1) shown in FIG. 2(a1)

Further, a polyamide compound wherein $R^2$ is a hydroxyl group in the polyamide compound of embodiment A1, is referred to in particular as an embodiment A1-A3243T, and as a preferable embodiment, there may be mentioned Ac-Py-Hp-Py-β-Im-Py-Py-γ-Im-Im-Py-β-Im-Py-Im-β-Dp (wherein, γ is γ-aminobutyric acid residue, Dp is N,N-dimethylaminopropyl residue, and the "residue" is conveniently abbreviated; hereinafter sometimes referred to as embodiment a1-A3243T). [0040]

As one embodiment of the polyamide compound which targets at the target double-stranded DNA of the above formula (14), there may be mentioned a polyamide compound (hereinafter sometimes referred to as embodiment A2) of the following formula (3):

[wherein, $R^1$ is a hydrogen atom, an alkyl group having 1 to 4 carbon atoms, a hydroxyl group, an amino group, a carboxyl group, or an acyl group having 1 to 4 carbon atoms, $R^2$ is independently a hydrogen atom, or a hydroxyl group, $R^3$, $R^6$, and $R^7$ are independently a hydrogen atom, an amino group, or —NH$_3$, $R^4$ is a single bond or β-alanine residue, $R^5$ is a hydroxyl group, or N-dimethylaminopropyl residue, and the hydrogen atom of the Im residue, Py residue, Hp residue, β residue, γ-aminobutyric acid residue, or (R) 2,4-diaminobutyric acid residue may be substituted with an alkyl group having 1 to 4 carbon atoms, an amino group, a hydroxyl group, or a carboxyl group]. As a further preferable embodiment A2, there may be mentioned Ac-Im-Im-Im-β-Py-Py-β-Im-Py-Py-γ-Im-Im-Py-β-Im-Py-Im-β-Py-Py-β-Dp (wherein, γ is γ-aminobutyric acid residue, Dp is N,N-dimethylaminopropyl residue, and the "residue" is abbreviated conveniently; hereinafter sometimes referred to as an embodiment a2) shown in FIG. 2(a2) Further, a polyamide compound wherein $R^2$ is hydroxyl group in the polyamide compound of embodiment A2, is particularly referred to as an embodiment A2-A3243T, and as a preferable embodiment, there may be mentioned Ac-Im-Im-Im-β-Hp-Py-β-Im-Py-Py-γ-Im-Im-Py-β-Im-Py-Im-β-Py-Py-β-Dp (wherein, γ is γ-aminobutyric acid residue, Dp is N,N-dimethylaminopropyl residue, and the "residue" is conveniently abbreviated; hereinafter sometimes referred to as embodiment a2-A3243T).

As one embodiment of the polyamide compound which targets at the target double-stranded DNA of the above formula (15), there may be mentioned a polyamide compound (hereinafter sometimes referred to as an embodiment A3) of the following formula (4):

[Chem. 35]

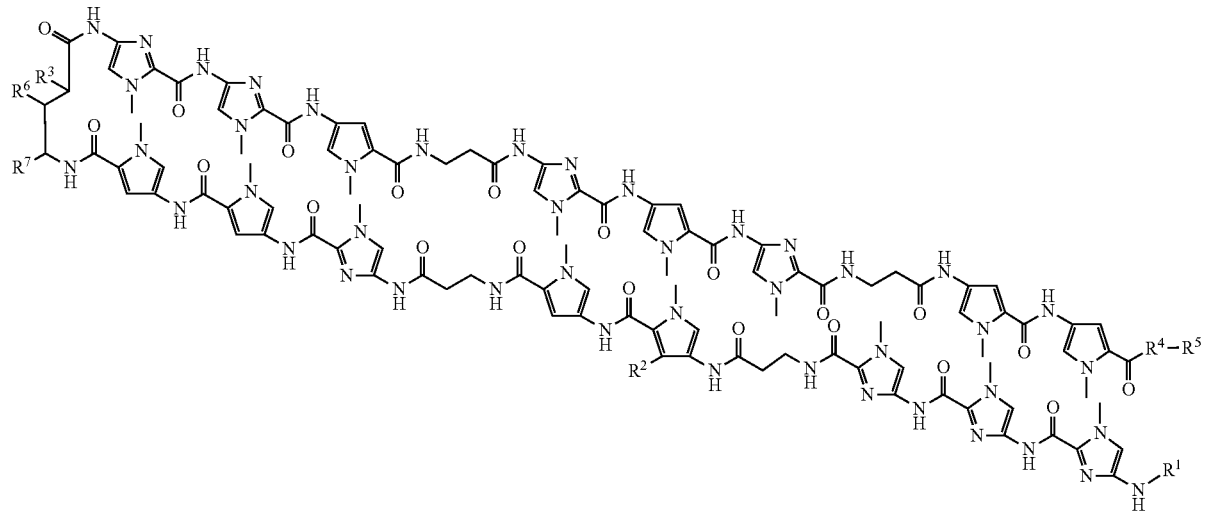

(3)

[Chem. 36]

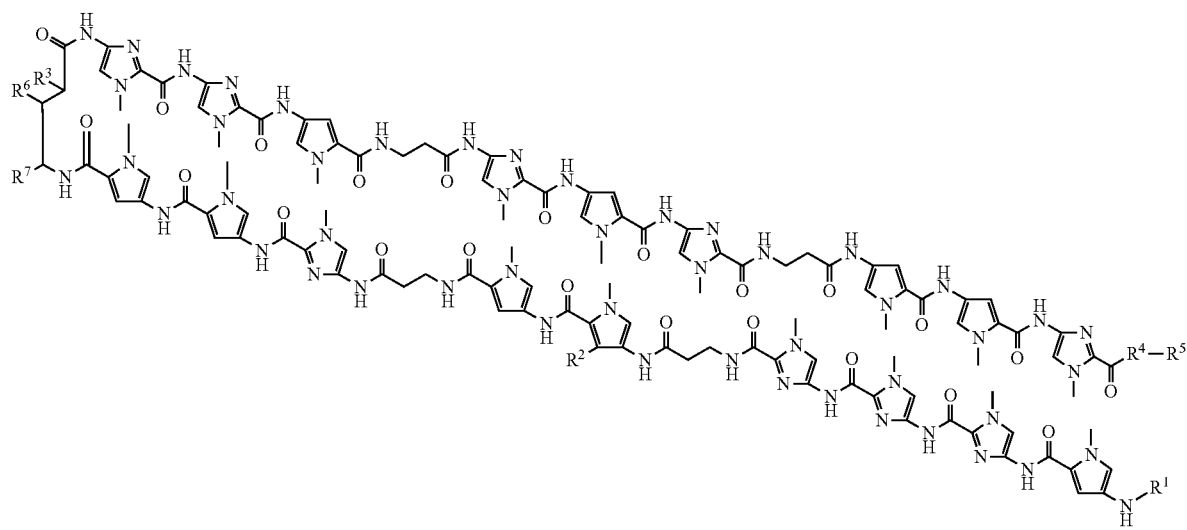

(4)

[wherein, $R^1$ is a hydrogen atom, an alkyl group having 1 to 4 carbon atoms, a hydroxyl group, an amino group, a carboxyl group, or an acyl group having 1 to 4 carbon atoms, $R^2$ is independently a hydrogen atom, or a hydroxyl group, $R^1$, $R^6$, and $R^7$ are independently a hydrogen atom, an amino group, or —$NH_3$, $R^4$ is a single bond or -alanine residue, $R^5$ is a hydroxyl group, or N-dimethylaminopropyl residue, and the hydrogen atom of the Im residue, Py residue, Hp residue, β residue, γ-aminobutyric acid residue, or (R) 2,4-diaminobutyric acid residue may be substituted with an alkyl group having 1 to 4 carbon atoms, an amino group, a hydroxyl group, or a carboxyl group]. As a further preferable embodiment A3, there may be mentioned Ac-Py-Im-Im-Im-β-Py-Py-β-Im-Py-Py-γ-Im-Im-Py-β-Im-Py-Im-β-Py-Py-Im-β-Dp (wherein, γ is γ-aminobutyric acid residue, Dp is N,N-dimethylaminopropyl residue, and the "residue" is abbreviated conveniently; hereinafter sometimes referred to as an embodiment a3) shown in FIG. 2(a3)

Further, a polyamide compound wherein $R^2$ is hydroxyl group in the polyamide compound of embodiment A3, is referred to in particular as an embodiment A3-A3243T, and as a preferable embodiment, there may be mentioned Ac-Py-Im-Im-Im-β-Hp-Py-β-Im-Py-Py-γ-Im-Im-Py-β-Im-Py-Im-β-Py-Py-Im-β-Dp (wherein, γ is γ-aminobutyric acid residue, Dp is N,N-dimethylaminopropyl residue, and the "residue" is conveniently abbreviated; hereinafter sometimes referred to as embodiment a3-A3243T).

As one embodiment of the polyamide compound which targets at the target double-stranded DNA of the above formula (16), there may be mentioned a polyamide compound (hereinafter sometimes referred to as embodiment B1) of the following formula (5):

[Chem. 37]

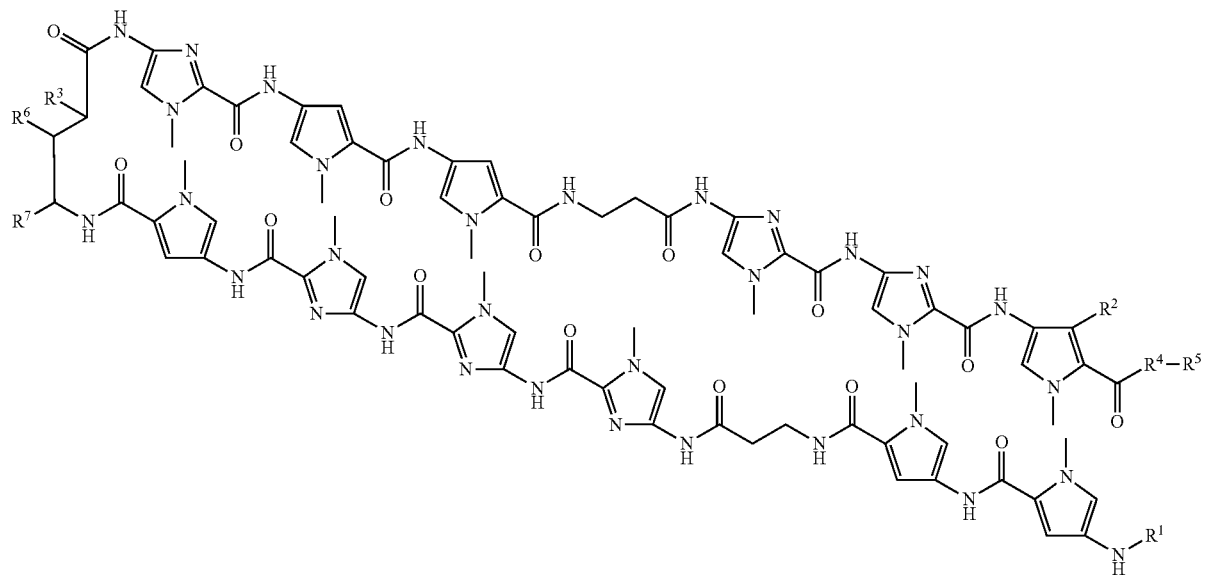

(5)

[wherein, R¹ is a hydrogen atom, an alkyl group having 1 to 4 carbon atoms, a hydroxyl group, an amino group, a carboxyl group, or an acyl group having 1 to 4 carbon atoms, R² is independently a hydrogen atom, or a hydroxyl group, R¹, R⁶, and R⁷ are independently a hydrogen atom, an amino group, or —NH₃, R⁴ is a single bond or -alanine residue, R⁵ is a hydroxyl group, or N-dimethylaminopropyl residue, and the hydrogen atom of the Im residue, Py residue, Hp residue, β residue, γ-aminobutyric acid residue, or (R) 2,4-diaminobutyric acid residue may be substituted with an alkyl group having 1 to 4 carbon atoms, an amino group, a hydroxyl group, or a carboxyl group], and more preferably, there may be mentioned Ac-Py-Py-β-Im-Im-Im-Py-γ-Im-Py-Py-β-β-Im-Im-Py-β-Dp (wherein, γ is γ-aminobutyric acid residue, Dp is N,N-dimethylaminopropyl residue, and the "residue" is conveniently abbreviated; hereinafter sometimes referred to as embodiment b1) shown in FIG. 2(b1).

As one embodiment of the polyamide compound which targets at the target double-stranded DNA of the above formula (17), there may be mentioned a polyamide compound (hereinafter sometimes referred to as embodiment B2) of the following formula (6):

[Chem. 38]

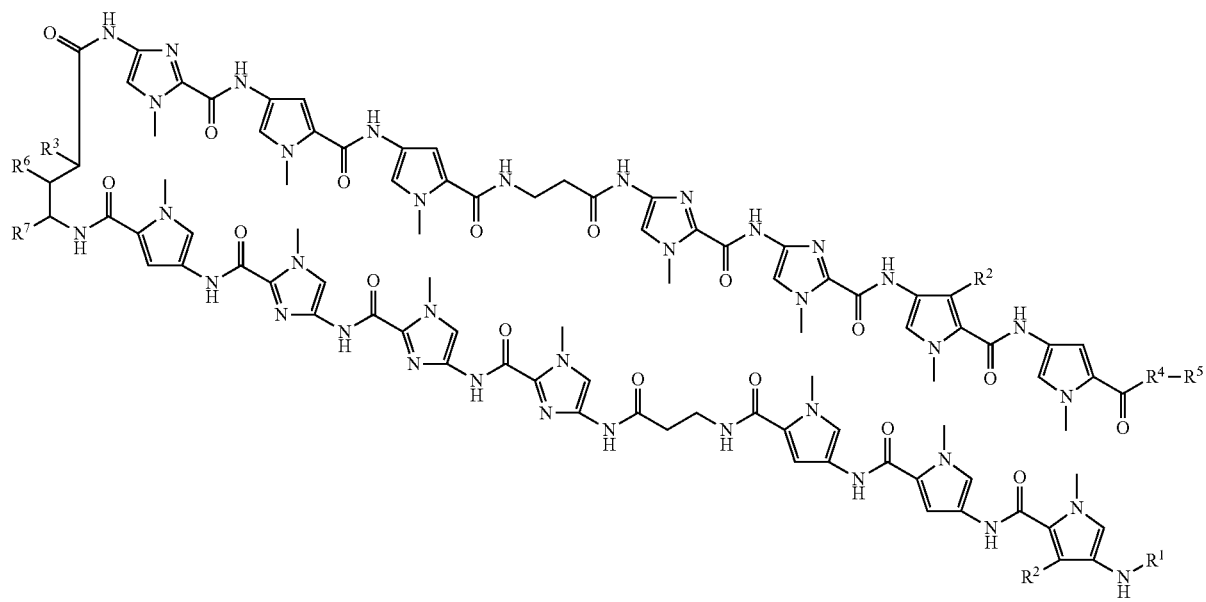

(6)

[wherein, $R^1$ is a hydrogen atom, an alkyl group having 1 to 4 carbon atoms, a hydroxyl group, an amino group, a carboxyl group, or an acyl group having 1 to 4 carbon atoms, $R^2$ is independently a hydrogen atom, or a hydroxyl group, $R^3$, $R^6$, and $R^7$ are independently a hydrogen atom, an amino group, or —$NH_3$, $R^4$ is a single bond or β-alanine residue, $R^5$ is a hydroxyl group, or N-dimethylaminopropyl residue, and the hydrogen atom of the Im residue, Py residue, Hp residue, β residue, γ-aminobutyric acid residue, or (R) 2,4-diaminobutyric acid residue may be substituted with an alkyl group having 1 to 4 carbon atoms, an amino group, a hydroxyl group, or a carboxyl group], and more preferably, there may be mentioned Ac-Py-Py-Py-β-Im-Im-Im-Py-γ-Im-Py-Py-β-Im-Im-Py-Py-β-Dp (wherein, γ is γ-aminobutyric acid residue, Dp is N,N-dimethylaminopropyl residue, and the "residue" is conveniently abbreviated; hereinafter sometimes referred to as embodiment b2) shown in FIG. 2(b2).

As one embodiment of the polyamide compound which targets at the target double-stranded DNA of the above formula (18), there may be mentioned a polyamide compound (hereinafter sometimes referred to as embodiment C1) of the following formula (7):

[wherein, $R^1$ is a hydrogen atom, an alkyl group having 1 to 4 carbon atoms, a hydroxyl group, an amino group, a carboxyl group, or an acyl group having 1 to 4 carbon atoms, $R^2$ is independently a hydrogen atom, or a hydroxyl group, $R^1$, $R^6$, and $R^7$ are independently a hydrogen atom, an amino group, or —$NH_3$, $R^4$ is a single bond or β-alanine residue, $R^5$ is a hydroxyl group, or N-dimethylaminopropyl residue, and the hydrogen atom of the Im residue, Py residue, Hp residue, β residue, γ-aminobutyric acid residue, or (R) 2,4-diaminobutyric acid residue may be substituted with an alkyl group having 1 to 4 carbon atoms, an amino group, a hydroxyl group, or a carboxyl group], and more preferably, there may be mentioned Ac-Py-Im-Im-β-Py-Im-γ-Py-Py-Im-β-Py-Py-β-Dp (wherein, γ is γ-aminobutyric acid residue, Dp is N,N-dimethylaminopropyl residue, and the "residue" is conveniently abbreviated; hereinafter sometimes referred to as embodiment c1) shown in FIG. 2(c).

As one embodiment of the polyamide compound which targets at the target double-stranded DNA of the above formula (19), there may be mentioned a polyamide compound (hereinafter sometimes referred to as embodiment C2) of the following formula (8):

[Chem. 39]

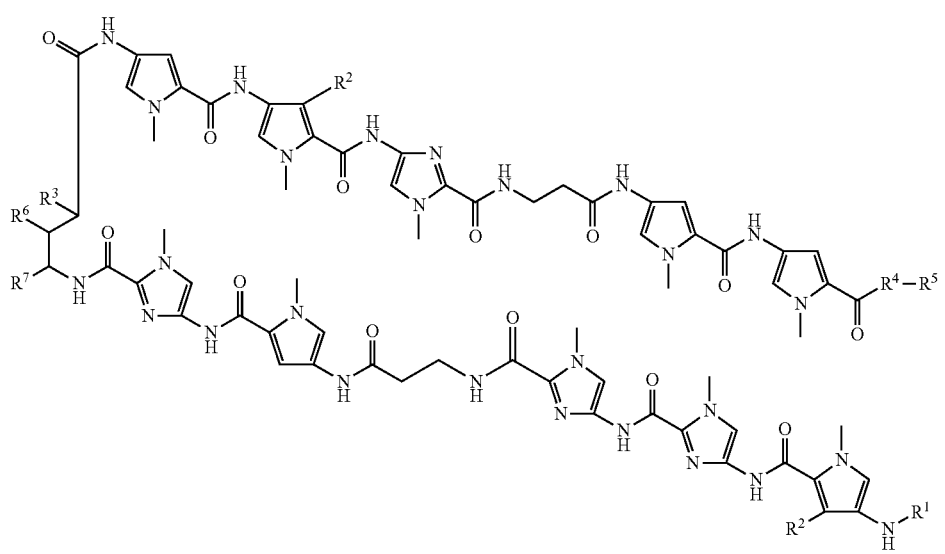

(7)

[Chem. 40]

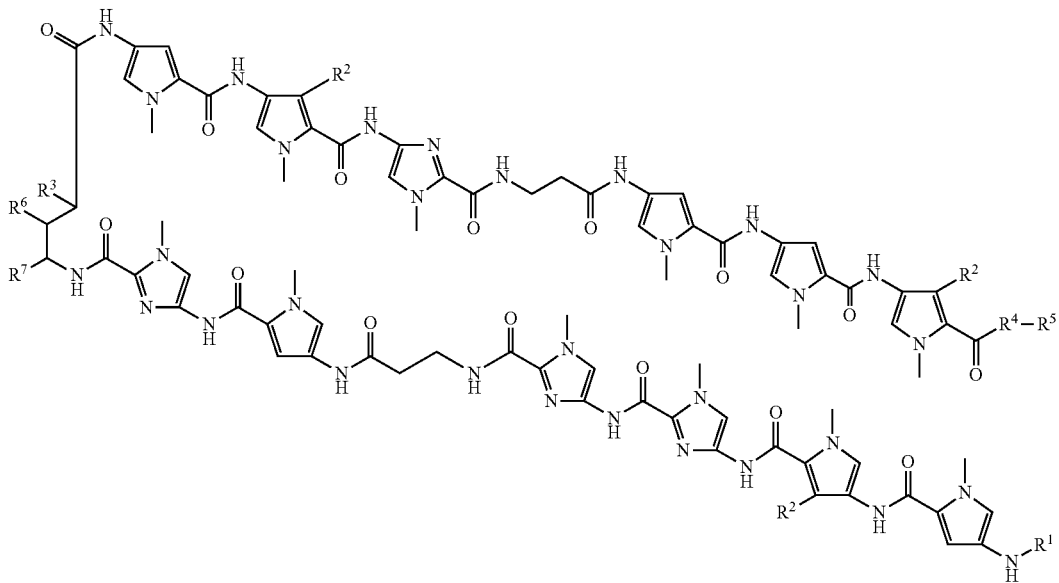

(8)

[wherein, $R^1$ is a hydrogen atom, an alkyl group having 1 to 4 carbon atoms, a hydroxyl group, an amino group, a carboxyl group, or an acyl group having 1 to 4 carbon atoms, $R^2$ is independently a hydrogen atom, or a hydroxyl group, $R^1$, $R^6$, and $R^7$ are independently a hydrogen atom, an amino group, or —$NH_3$, $R^4$ is a single bond or β-alanine residue, $R^5$ is a hydroxyl group, or N-dimethylaminopropyl residue, and the hydrogen atom of the Im residue, Py residue, Hp residue, β residue, γ-aminobutyric acid residue, or (R) 2,4-diaminobutyric acid residue may be substituted with an alkyl group having 1 to 4 carbon atoms, an amino group, a hydroxyl group, or a carboxyl group], and more preferably, there may be mentioned Ac-Py-Py-Im-Im-β-Py-Im-γ-Py-Py-Im-β-Py-Py-Py-β-Dp (wherein, γ is γ-aminobutyric acid residue, Dp is N,N-dimethylaminopropyl residue, and the "residue" is conveniently abbreviated; hereinafter sometimes referred to as embodiment c2) shown in FIG. 2(*c*2).

As one embodiment of the polyamide compound which targets at the target double-stranded DNA of the above formula (20), there may be mentioned a polyamide compound (hereinafter sometimes referred to as embodiment D1) of the following formula (9):

[Chem. 41]

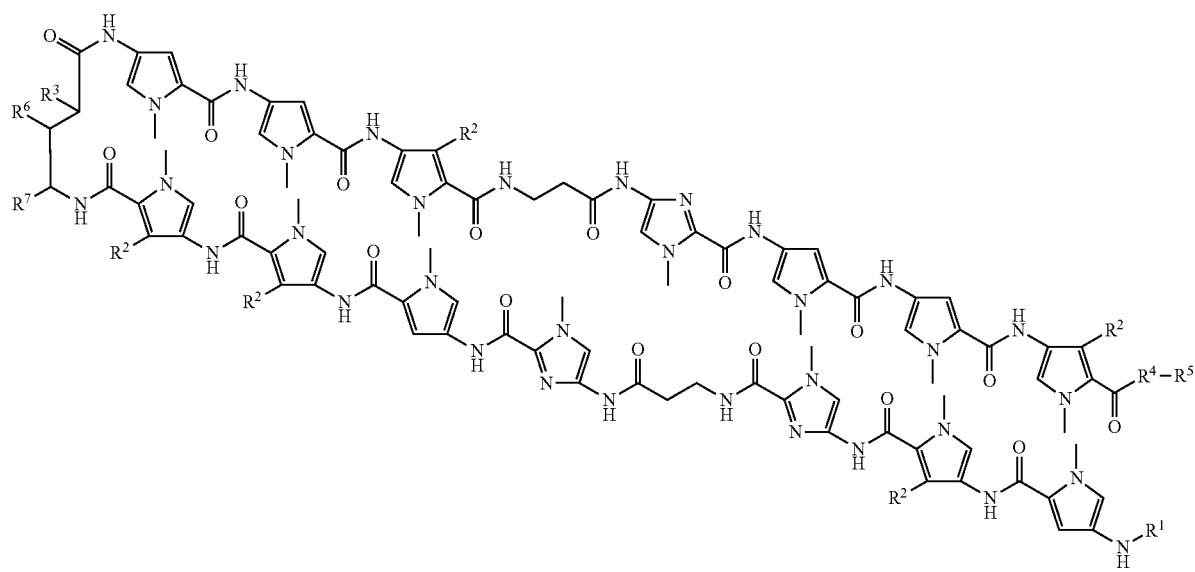

(9)

[wherein, R¹ is a hydrogen atom, an alkyl group having 1 to 4 carbon atoms, a hydroxyl group, an amino group, a carboxyl group, or an acyl group having 1 to 4 carbon atoms, R² is independently a hydrogen atom, or a hydroxyl group, R¹, R⁶, and R⁷ are independently a hydrogen atom, an amino group, or —NH₃, R⁴ is a single bond or β-alanine residue, R⁵ is a hydroxyl group, or N-dimethylaminopropyl residue, and the hydrogen atom of the Im residue, Py residue, Hp residue, β residue, γ-aminobutyric acid residue, or (R) 2,4-diaminobutyric acid residue may be substituted with an alkyl group having 1 to 4 carbon atoms, an amino group, a hydroxyl group, or a carboxyl group]. However the target double-stranded DNA represented by the formula (20) contains adenine (A) and thymine (T) in abundance. Thus, Hp residue is preferable as a residue corresponding to T. That is, the hydroxyl group is preferable for R². As for the specific polyamide compound, there may be mentioned, for example Ac-Py-Py-Im-β-Im-Py-Py-Py-γ-Py-Py-Py-β-Im-Py-Py-Py-β-Dp (wherein, γ is a γ-aminobutyric acid residue, Dp is a N,N-dimethylaminopropyl residue, and the "residue" is conveniently abbreviated; hereinafter sometimes referred to as embodiment d1) shown in FIG. 2(d1) and Ac-Py-Hp-Im-β-Im-Py-Hp-Hp-γ-Py-Py-Hp-β-Im-Py-Py-Hp-β-Dp (wherein, γ is a γ-aminobutyric acid residue, Dp is a N,N-dimethylaminopropyl residue, and the "residue" is conveniently abbreviated; hereinafter sometimes referred to as embodiment d1-Hp). The embodiment d1-Hp is more preferable.

As one embodiment of the polyamide compound which targets at the target double-stranded DNA of the above formula (21), there may be mentioned a polyamide compound (hereinafter sometimes referred to as embodiment E1) of the following formula (10):

[Chem. 42]

[wherein, 1e is a hydrogen atom, an alkyl group having 1 to 4 carbon atoms, a hydroxyl group, an amino group, a carboxyl group, or an acyl group having 1 to 4 carbon atoms, 1e is independently a hydrogen atom, or a hydroxyl group, R¹, R⁶, and R⁷ are independently a hydrogen atom, an amino group, or —NH₃, R⁴ is a single bond or β-alanine residue, R⁵ is a hydroxyl group, or N-dimethylaminopropyl residue, and the hydrogen atom of the Im residue, Py residue, Hp residue, β residue, γ-aminobutyric acid residue, or (R) 2,4-diaminobutyric acid residue may be substituted with an alkyl group having 1 to 4 carbon atoms, an amino group, a hydroxyl group, or a carboxyl group]. However the target double-stranded DNA represented by the formula (21) contains adenine (A) and thymine (T) in abundance. Thus, Hp residue is preferable as a residue corresponding to T. That is, the hydroxyl group is preferable for R². As for the specific polyamide compound, there may be mentioned, for example Ac-Py-Py-Py-Im-β-Im-Py-Py-γ-Py-Py-Py-Im-β-Py-Py-Py-β-Dp (wherein, γ is a γ-aminobutyric acid residue, Dp is N,N-dimethylaminopropyl residue, and the "residue" is conveniently abbreviated; hereinafter sometimes referred to as embodiment e1) shown in FIG. 2(e1) and Ac-Hp-Py-Hp-Im-β-Im-Py-Hp-γ-Py-Hp-Py-Im-β-Py-Hp-Py-β-Dp (wherein, γ is a γ-aminobutyric acid residue, Dp is a N,N-dimethylaminopropyl residue, and the "residue" is conveniently abbreviated; hereinafter sometimes referred to as embodiment e1-Hp). The embodiment e1-Hp is more preferable.

As one embodiment of the polyamide compound which targets at the target double-stranded DNA of the above formula (22), there may be mentioned a polyamide compound (hereinafter sometimes referred to as embodiment F1) of the following formula (11):

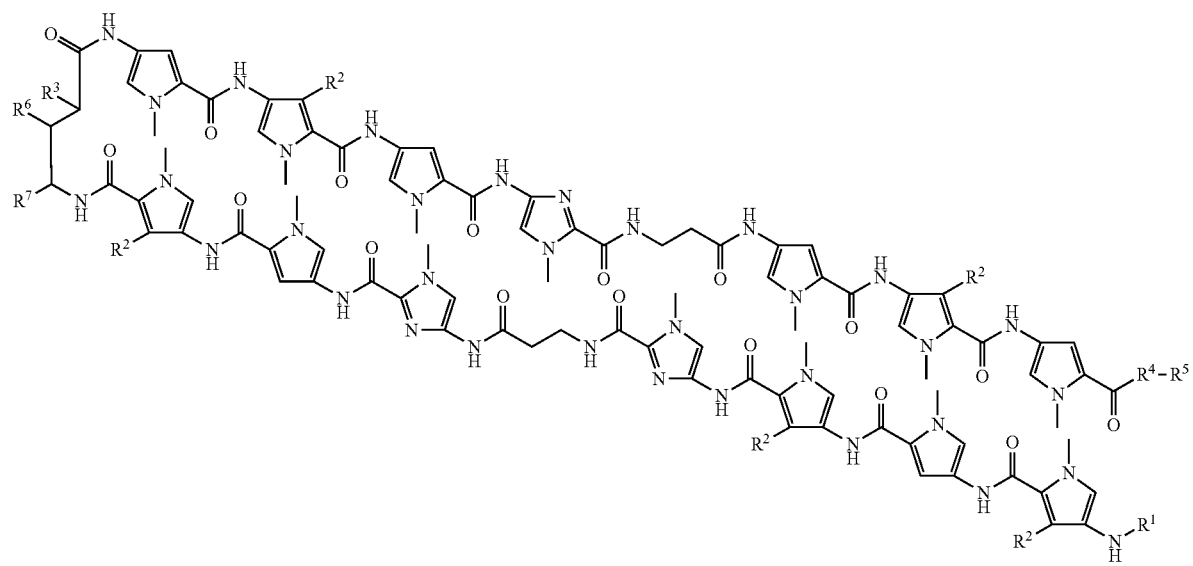

(10)

[Chem. 43]

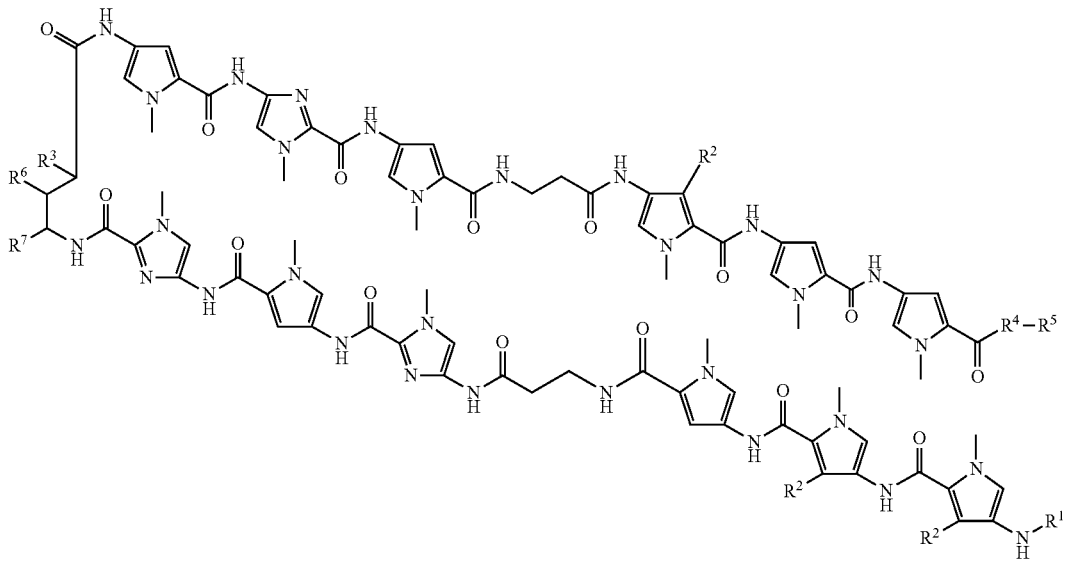

(11)

[wherein, $R^1$ is a hydrogen atom, an alkyl group having 1 to 4 carbon atoms, a hydroxyl group, an amino group, a carboxyl group, or an acyl group having 1 to 4 carbon atoms, $R^2$ is independently a hydrogen atom, or a hydroxyl group, $R^1$, $R^6$, and $R^7$ are independently a hydrogen atom, an amino group, or —NH$_3$, $R^4$ is a single bond or β-alanine residue, $R^5$ is a hydroxyl group, or N-dimethylaminopropyl residue, and the hydrogen atom of the Im residue, Py residue, Hp residue, β residue, γ-aminobutyric acid residue, or (R) 2,4-diaminobutyric acid residue may be substituted with an alkyl group having 1 to 4 carbon atoms, an amino group, a hydroxyl group, or a carboxyl group]. However the target double-stranded DNA represented by the formula (22) contains adenine (A) and thymine (T) in abundance. Thus, Hp residue is preferable as a residue corresponding to T. That is, the hydroxyl group is preferable for $R^2$. As for the specific polyamide compound, there may be mentioned, for example Ac-Py-Py-Py-β-Im-Py-Im-γ-Py-Im-Py-β-Py-Py-Py-β-Dp (wherein, γ is a γ-aminobutyric acid residue, Dp is a N,N-dimethylaminopropyl residue, and the "residue" is conveniently abbreviated; hereinafter sometimes referred to as embodiment f1) shown in FIG. 2(f1) and Ac-Hp-Hp-Py-β-Im-Py-Im-γ-Py-Im-Py-β-Hp-Py-Py-β-Dp (wherein, γ is a γ-aminobutyric acid residue, Dp is a N,N-dimethylaminopropyl residue, and the "residue" is conveniently abbreviated; hereinafter sometimes referred to as embodiment f1-Hp). The embodiment f1-Hp is more preferable.

$R^1$ is a hydrogen atom, an alkyl group having 1 to 4 carbon atoms, a hydroxyl group, an amino group, a carboxyl group, or an acyl group having 1 to 4 carbon atoms, but preferably an acetyl group of the following formula (30):

[Chem. 44]

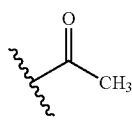

(30)

$R^2$ is independently a hydrogen atom, or a hydroxyl group. When $R^2$ is a hydrogen atom, $R^2$-binding residue is Py residue. When $R^2$ is a hydroxyl group, the $R^2$-binding residue is an Hp residue.

$R^3$, $R^6$, and $R^7$ are independently a hydrogen atom, an amino group, or —NH$_3$. When $R^3$, $R^6$, and $R^7$ are hydrogen atoms, $R^3$-, $R^6$-, and $R^7$-binding residues are 7-aminobutyric acid residues. When $R^3$ is an amino group, and $R^6$ and $R^7$ are hydrogen atoms, $R^3$-, $R^6$-, and $R^7$-binding residues are (R) 2,4-diaminobutyric acid residues. Further, $R^3$, $R^6$, and $R^7$ independently may be —NH$_3$ of the formula (32):

[Chem. 45]

⋯⋯NH$_3$.

(32)

When $R^3$, $R^6$, and $R^7$ are —NH$_3$, the polyamide compound has a positive charge, and easily binds to DNA. Thus, it is preferable.

$R^4$ is a single bond, or a jβ-alanine residue of formula (26):

[Chem. 46]

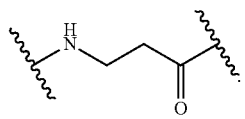

(26)

$R^5$ is a hydroxyl group or a N,N-dimethylaminopropyl of formula (33):

[Chem. 47]

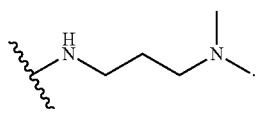

(33)

A hydrogen atom of the Im residue, Py residue, Hp residue, or β residue, can be substituted with an alkyl group having 1 to 4 carbon atoms, an amino group, a hydroxyl group, or a carboxyl group. However, a hydrogen atom is preferable. Further, a hydrogen atom of a γ-aminobutyric acid residue, (R) 2,4-diaminobutyric acid residue, or 5-aminovaleric acid residue may be substituted with an alkyl group having 1 to 4 carbon atoms, an amino group, a hydroxyl group, or a carboxyl group, or —NH$_3$. However, a hydrogen atom or —NH$_3$ is preferable.

(ML1 Polyamide)

The preferable "embodiment a1" in embodiment A1 is ML1 polyamide of the following formula (12):

[Chem. 48]

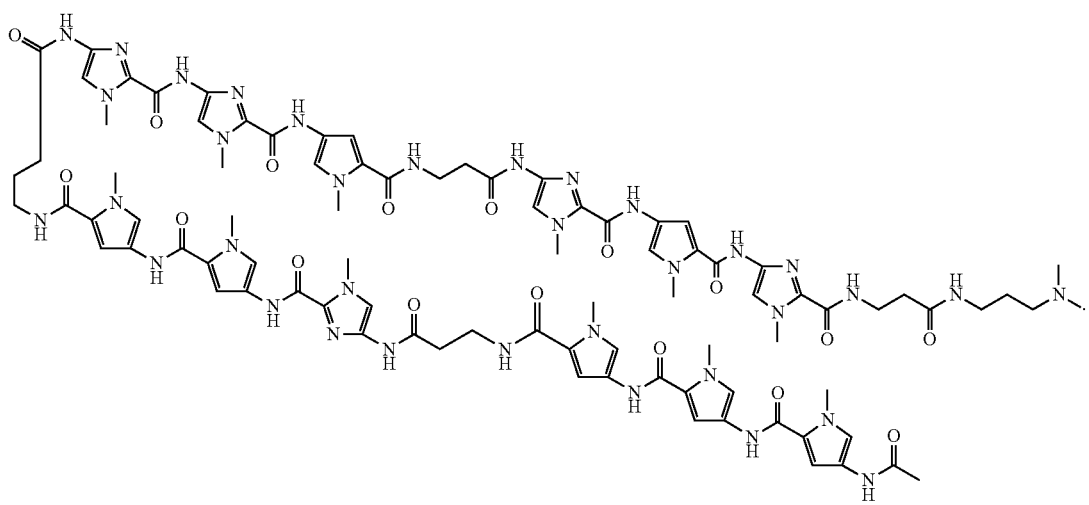

(12)

(Synthesis Method of Polyamide Compound)

The polyamide compound of the present invention can be synthesized by the Fmoc method. The Fmoc method is a solid-phase peptide synthesis method using Fmoc (9fluorenylmethyloxycarbonyl), and commercially available peptide Synthesizers may be used.

For example, NovaPEG Wang Resin is used as a solid-phase. Then, Py, Im, β-alanine, or the like is added thereto through a dehydration synthesis (amide binding), and a length of chains is sequentially extended. After a synthesis of the polyamide compound of interest is finished, N,N-dimethyl-1,3-propanediamine is added thereto. Then, the polyamide compound on the surface of the solid-phase is cleaved at around 60'C and then collected.

[2] Agent for Promoting Replication of Wild-Type mtDNA

An agent for promoting replication of wild-type mtDNA of the present invention comprises the polyamide compound of the present invention, or a pharmaceutically acceptable salt thereof, as an active ingredient.

The polyamide compound within the agent for promoting replication of wild-type mtDNA is not particularly limited, so long as it is the polyamide compound described in the above paragraph "[1] Polyamide compound". The all-polyamide compound as mentioned above may be used.

When the agent for promoting replication of wild-type mtDNA of the present invention is administered to mitochondrial genetic diseases patients or normal subjects (animals, particularly humans), a replication of wild-type mtDNA can be promoted. In particular, in mitochondrial genetic disease patients, mitochondrial genetic disease is prevented and treated by selectively promoting the replication of wild-type mtDNA.

The formulation of the agent for promoting replication of wild-type mtDNA of the present invention is not limited. However, there may be mentioned oral agents, such as powders, subtle granules, granules, tablets, capsules, suspensions, emulsions, sylups, extracts, or balls; or parentarnal agents, such as injections, liquids for external use, ointments, suppositorys, creams for local administration, or eye-drops.

The above oral agent can be prepared in accordance with conventional methods, using fillers, such as gelatin, alginate sodium, starch, cornstarch, saccharose, lactose, glucose, mannitol, carboxymethyl-cellulose, dextrin, polyvinyl pyrrolidone, clystalline cellulose, soy lecithin, sucrose, fatty acid ester, talc, magnesium stearate, polyethylene glycol, magnesium silicate, silicic anhydride, or synthetic aluminum silicate; binders, disintegrators, detergents, lubricants, flow accelerators, diluents, preservatives, colorants, flavors, correctives, stabilizers, humectants, antiseptics, antioxidant, or the like.

Examples of the parentarnal administration include injection (for example, subcutaneous injection or intravenous injection), rectal administration, or the like. Among these, the injections are preferred.

For example, in preparing the injections, an aqueous solvent such as a normal saline solution or Ringer solution, non-aqueous solutions such as plant oil or fatty acid ester, a tonicity agent such as glucose or sodium chloride, a solubility assisting agent, a stabilizing agent, an antiseptic agent, a suspending agent, or an emulsifying agent, may be optionally used, in addition to the active ingredient.

Further, the agent of the present invention may be administered by means of sustained-release formulation using a sustained-release polymer. For example, the agent of the present invention is introduced into a pellet of ethylene vinyl acetate polymer, and then the pellet can be surgically implanted into a tissue for either treatment or prevention.

The agent for promoting replication of wild-type mtDNA of the present invention may contain, but is not limited to, 0.01 to 99% by weight, preferably 0.1 to 80% by weight, of the active ingredient.

A dose of the agent for promoting replication of wild-type mtDNA of the present invention may be appropriately determined in accordance with, for example, age, sex, body weight, or degree of symptom of each patient, the type of each active ingredient, type of each disease, route of administration, or the like, and the determined dosage can be administered orally or parenterally.

In addition, the dosage form for administration of the agent for promoting replication of wild-type mtDNA of the present invention is not limited to a drug medicine. That is, it can be administered as food and drink of various form, such as functional food, healthy food (including drink), or animal food.

[3] Pharmaceutical Composition

A pharmaceutical composition of the present invention comprises the polyamide compound of the present invention, or a pharmaceutically acceptable salt thereof, as an active ingredient. The polyamide compound within the pharmaceutical composition of the present invention is not particularly limited, so long as it is the polyamide compound described in the above paragraph "[1] Polyamide compound". The all-polyamide compound as mentioned above may be used.

The pharmaceutical composition of the present invention can be comprised of one or more of the polyamide compounds. The pharmaceutical composition of the present invention may be one dosage form, two dosage forms, or more. For example, when two or more polyamide compounds are contained in the pharmaceutical composition, two or more polyamide compounds may be provided as a dosage form, or two or more dosage forms.

(Pharmaceutical Composition for Treating or Preventing Mitochondrial Genetic Disease)

The pharmaceutical composition of the present invention can be used for treating or preventing mitochondrial genetic diseases. In the mitochondrial genetic diseases such as MELAS, mutant mtDNA and wild-type (normal-type) mtDNA coexist in a cell. This state of the cell is referred as a heteroplasmy. When the amount of the mutant mtDNA in the cell excesses a certain level or more (i.e. 60% to 95%), mitochondrial genetic diseases such as MELAS onset. The pharmaceutical composition of the present invention can shift a heteroplasmy wherein the wild-type mtDNA is dominant to wild-type mtDNA, and whereby the development of the mitochondrial genetic diseases can be avoided. Furthermore, in the case that a rate of the mutant mtDNA does not exceed the threshold level, and thus the mitochondrial genetic diseases are developed, the pharmaceutical composition of the present invention can suppress a shift of a heteroplasmy wherein the mutant mtDNA is dominant, by administration of the pharmaceutical composition of the present invention. Therefore, the pharmaceutical composition of the present invention is effective for preventing development of the mitochondrial genetic diseases.

(Pharmaceutical Composition for Treating or Preventing Mitochondrial Genetic Diseases)
(Mitochondrial Genetic Disease Caused by the A3236G Mutation)

A mitochondrial genetic disease caused by the A3236G mutation is present with symptoms of sporadic bilateral optic neuropathy.

The mitochondrial genetic disease caused by the A3236G mutation can be treated or prevented by a pharmaceutical composition comprising a polyamide compound having a residue binding to an A/T pair consisting of the first A of the sense-stranded DNA 5'-ATGGCAGAGCCCGGTAATCG-CATAA-3' (SEQ ID NO: 1), and the corresponding T. For example, the mitochondrial genetic disease caused by the A3236G mutation can be treated or prevented by the pharmaceutical composition comprising the polyamide compound of embodiment C2.

(Mitochondrial Genetic Diseases Caused by the A3243G Mutation)

Mitochondrial genetic diseases caused by the A3243G mutation are present with symptoms of mitochondrial myopathy, encephalopathy, lactic acidosis, stroke-like episodes; diabetes and hypacusia; mitochondrial myopathy; Leigh's syndrome; sensory deafness; chronic progressive external ophthalmoplegia; diabetes with matricliny hypacusia; or focal segmental glomerulosclerosis.

The mitochondrial genetic diseases caused by the A3243G mutation can be treated or prevented by a pharmaceutical composition comprising a polyamide compound having a residue binding to an A/T pair consisting of the eighth A of the sense-stranded DNA 5'-ATGGCAGAGC-CCGGTAATCGCATAA-3' (SEQ ID NO: 1), and the corresponding T. For example, the mitochondrial genetic diseases caused by the A3243G mutation can be treated or prevented by the pharmaceutical composition comprising the polyamide compound of embodiment A1, A2, A3, B1, B2, C1 or C2.

(Mitochondrial Genetic Diseases Caused by the A3243T Mutation)

Mitochondrial genetic diseases caused by the A3243T mutation are present with symptoms of mitochondrial myopathy, encephalopathy, lactic acidosis, stroke-like episodes; mitochondrial myopathy; sensory deafness; or chronic progressive external ophthalmoplegia.

The mitochondrial genetic diseases caused by the A3243T mutation can be treated or prevented by a pharmaceutical composition comprising a polyamide compound wherein it has a residue binding to an A/T pair consisting of the eighth A of the sense-stranded DNA 5'-ATGGCAGAGCCCGG-TAATCGCATAA-3' (SEQ ID NO: 1) and the corresponding T; and the residue corresponding to T of the A/T pair is an Hp residue. For example, the mitochondrial genetic diseases caused by the A3243T mutation can be treated or prevented by the pharmaceutical composition comprising the polyamide compound of embodiment A1-A3243T, A2-A3243T or A3-A3243T.

(Mitochondrial Genetic Disease Caused by the G3244A Mutation)

A mitochondrial genetic disease caused by the G3244A mutation is present with symptoms of mitochondrial myopathy, encephalopathy, lactic acidosis, stroke-like episodes.

The mitochondrial genetic disease caused by the G3244A mutation can be treated or prevented by a pharmaceutical composition comprising a polyamide compound having a residue binding to a G/C pair consisting of the ninth G of the sense-stranded DNA 5'-ATGGCAGAGCCCGGTAATCG-CATAA-3' (SEQ ID NO: 1), and the corresponding C. For example, the mitochondrial genetic disease caused by the G3244A mutation can be treated or prevented by the pharmaceutical composition comprising the polyamide compound of embodiment A1, A2, A3, B1 or B2.

(Mitochondrial Genetic Disease Caused by the G3249A Mutation)

A mitochondrial genetic disease caused by the G3249A mutation is present with symptoms of Kearns-Sayre syndrome.

The mitochondrial genetic disease caused by the G3249A mutation can be treated or prevented by a pharmaceutical composition comprising a polyamide compound having a residue binding to a G/C pair consisting of the fourteenth G of the sense-stranded DNA 5'-ATGGCAGAGCCCGG-TAATCGCATAA-3' (SEQ ID NO: 1), and the corresponding C. For example, the mitochondrial genetic disease caused by the G3249A mutation can be treated or prevented by the pharmaceutical composition comprising the polyamide compound of embodiment B1 or B2.

(Mitochondrial Genetic Diseases Caused by the T3250C Mutation)

Mitochondrial genetic diseases caused by the T3250C mutation are present with symptoms of mitochondrial myopathy or chronic progressive external ophthalmoplegia.

The mitochondrial genetic diseases caused by the T3250C mutation can be treated or prevented by a pharmaceutical composition comprising a polyamide compound having a residue binding to a T/A pair consisting of the fifteenth T of the sense-stranded DNA 5'-ATGGCAGAGCCCGG-TAATCGCATAA-3' (SEQ ID NO: 1), and the corresponding A. For example, the mitochondrial genetic diseases caused by the T3250C mutation can be treated or prevented by the pharmaceutical composition comprising the polyamide compound of embodiment B1, B2 or D1.

(Mitochondrial Genetic Disease Caused by the A3251G Mutation)

A mitochondrial genetic disease caused by the A3251G mutation is present with symptoms of mitochondrial myopathy.

The mitochondrial genetic disease caused by the A3251G mutation can be treated or prevented by a pharmaceutical composition comprising a polyamide compound having a residue binding to an A/T pair consisting of the sixteenth A of the sense-stranded DNA 5'-ATGGCAGAGCCCGG-TAATCGCATAA-3' (SEQ ID NO: 1), and the corresponding T. For example, the mitochondrial genetic disease caused by the A3251G mutation can be treated or prevented by the pharmaceutical composition comprising the polyamide compound of embodiment B1, D2 or E1.

(Mitochondrial Genetic Disease Caused by the A3252G Mutation)

A mitochondrial genetic disease caused by the A3252G mutation is present with symptoms of mitochondrial myopathy, encephalopathy, lactic acidosis, stroke-like episodes.

The mitochondrial genetic disease caused by the A3252G mutation can be treated or prevented by a pharmaceutical composition comprising a polyamide compound having a residue binding to an A/T pair consisting of the seventeenth A of the sense-stranded DNA 5'-ATGGCAGAGCCCGG-TAATCGCATAA-3' (SEQ ID NO: 1), and the corresponding T. For example, the mitochondrial genetic disease caused by the A3252G mutation can be treated or prevented by the pharmaceutical composition comprising the polyamide compound of embodiment D1 or E1.

(Mitochondrial Genetic Disease Caused by the C3254A Mutation)

A mitochondrial genetic disease caused by the C3254A mutation is present with symptoms of diabetes in pregnancy.

The mitochondrial genetic disease caused by the C3254A mutation can be treated or prevented by a pharmaceutical composition comprising a polyamide compound having a residue binding to a C/G pair consisting of the nineteenth C of the sense-stranded DNA 5'-ATGGCAGAGCCCGG-TAATCGCATAA-3' (SEQ ID NO: 1), and the corresponding G. For example, the mitochondrial genetic disease caused by the C3254A mutation can be treated or prevented by the pharmaceutical composition comprising the polyamide compound of embodiment D1, E1 or F1.

(Mitochondrial Genetic Disease Caused by the C3254G Mutation)

A mitochondrial genetic disease caused by the C3254G mutation is present with symptoms of mitochondrial myopathy.

The mitochondrial genetic disease caused by the C3254G mutation can be treated or prevented by a pharmaceutical composition comprising a polyamide compound having a residue binding to a C/G pair consisting of the nineteenth C of the sense-stranded DNA 5'-ATGGCAGAGCCCGG-TAATCGCATAA-3' (SEQ ID NO: 1), and the corresponding G. For example, the mitochondrial genetic disease caused by the C3254G mutation can be treated or prevented by the pharmaceutical composition comprising the polyamide compound of embodiment D1, E1 or F1.

(Mitochondrial Genetic Disease Caused by the G3255A Mutation)

A mitochondrial genetic disease caused by the G3255A mutation is present with symptoms of MERRF/KSS overlap syndrome.

The mitochondrial genetic disease caused by the G3255A mutation can be treated or prevented by a pharmaceutical composition comprising a polyamide compound having a residue binding to a G/C pair consisting of the twentieth G of the sense-stranded DNA 5'-ATGGCAGAGCCCGG-TAATCGCATAA-3' (SEQ ID NO: 1), and the corresponding C. For example, the mitochondrial genetic disease caused by the G3255A mutation can be treated or prevented by the pharmaceutical composition comprising the polyamide compound of embodiment D1, E1 or F1.

(Mitochondrial Genetic Diseases Caused by the C3256T Mutation)

Mitochondrial genetic diseases caused by the C3256T mutation are present with symptoms of mitochondrial myopathy, encephalopathy, lactic acidosis, stroke-like episodes/ myoclonic epilepsy with ragged-red fibers.

The mitochondrial genetic diseases caused by the C3256T mutation can be treated or prevented by a pharmaceutical composition comprising a polyamide compound having a residue binding to a C/G pair consisting of the twenty-first C of the sense-stranded DNA 5'-ATGGCAGAGCCCGG-TAATCGCATAA-3' (SEQ ID NO: 1), and the corresponding G. For example, the mitochondrial genetic diseases caused by the C3256T mutation can be treated or prevented by the pharmaceutical composition comprising the polyamide compound of embodiment D1, E1 or F1.

(Mitochondrial Genetic Diseases Caused by the T3258C Mutation)

Mitochondrial genetic diseases caused by the T3258C mutation are present with symptoms of mitochondrial myopathy, encephalopathy, lactic acidosis, stroke-like episodes/ myopathy.

The mitochondrial genetic diseases caused by the T3258C mutation can be treated or prevented by a pharmaceutical composition comprising a polyamide compound having a residue binding to a T/A pair consisting of the twenty-third T of the sense-stranded DNA 5'-ATGGCAGAGCCCGG-TAATCGCATAA-3' (SEQ ID NO: 1), and the corresponding A. For example, the mitochondrial genetic diseases caused by the T3258C mutation can be treated or prevented by the pharmaceutical composition comprising the polyamide compound of embodiment D1, E1 or F1.

(Mitochondrial Genetic Diseases Caused by the A3260G Mutation)

Mitochondrial genetic diseases caused by the A3260G mutation are present with symptoms of adult matricliny myopathy and cardiac myopathy.

The mitochondrial genetic diseases caused by the A3260G mutation can be treated or prevented by a pharmaceutical composition comprising a polyamide compound having a residue binding to an A/T pair consisting of the twenty-fifth A of the sense-stranded DNA 5'-ATGGCA-GAGCCCGGTAATCGCATAA-3' (SEQ ID NO: 1), and the corresponding T. For example, the mitochondrial genetic diseases caused by the A3260G mutation can be treated or prevented by the pharmaceutical composition comprising the polyamide compound of embodiment F1.

The formulation of the pharmaceutical composition of the present invention is not limited. However, there may be mentioned oral agents, such as powders, subtle granules, granules, tablets, capsules, suspensions, emulsions, sylups, extracts, or balls; or parentarnal agents, such as injections, liquids for external use, ointments, suppositorys, creams for local administration, or eye-drops.

The above oral agent can be prepared in accordance with conventional methods, using fillers, such as gelatin, alginate sodium, starch, cornstarch, saccharose, lactose, glucose, mannitol, carboxymethyl-cellulose, dextrin, polyvinyl pyrrolidone, clystalline cellulose, soy lecithin, sucrose, fatty acid ester, talc, magnesium stearate, polyethylene glycol, magnesium silicate, silicic anhydride, or synthetic aluminum silicate; binders, disintegrators, detergents, lubricants, flow accelerator, diluents, preservatives, colorants, flavors, correctives, stabilizers, humectants, antiseptics, antioxidant, or the like.

Examples of the parentarnal administration include injection (for example, subcutaneous injection or intravenous injection), rectal administration, or the like. Among these, injections are preferred.

For example, in preparing the injections, an aqueous solvent such as normal saline solution or Ringer solution, non-aqueous solutions such as plant oil or fatty acid ester, a tonicity agent such as glucose or sodium chloride, a solubility assisting agent, a stabilizing agent, an antiseptic agent, a suspending agent, or an emulsifying agent, may be optionally used, in addition to the active ingredient.

Further, the pharmaceutical composition of the present invention may be administered by means of sustained-release formulation using a sustained-release polymer. For example, the pharmaceutical composition of the present invention is introduced into a pellet of ethylene vinyl acetate polymer, and then the pellet can be surgically implanted into a tissue for treatment or prevention.

The pharmaceutical composition may contain, but is not limited to, 0.01 to 99% by weight, preferably 0.1 to 80% by weight, of the active ingredient.

A dose of the pharmaceutical composition of the present invention may be appropriately determined in accordance with, for example, age, sex, body weight, or degree of the symptoms of each patient, the type of each active ingredient, the type of each disease, the route of administration, or the like, and the determined dosage can be administered orally or parenterally.

In addition, dosage form for administration of the pharmaceutical composition of the present invention is not limited to a drug medicine. That is, it can be administered as food and drink of various form, such as a functional food, healthy food (including drink), or animal food.

The formulation of the medicine of the present invention is not limited. However, there may be mentioned oral agents, such as powders, subtle granules, granules, tablets, capsules, suspensions, emulsions, sylups, extracts, or balls; or parentarnal agents, such as injections, liquids for external use, ointments, suppositorys, creams for local administration, or eye-drops.

The above oral agent can be prepared in accordance with conventional methods, using fillers, such as gelatin, alginate sodium, starch, cornstarch, saccharose, lactose, glucose, mannitol, carboxymethyl-cellulose, dextrin, polyvinyl pyrrolidone, clystalline cellulose, soy lecithin, sucrose, fatty acid ester, talc, magnesium stearate, polyethylene glycol, magnesium silicate, silicic anhydride, or synthetic aluminum silicate; binders, disintegrators, detergents, lubricants, flow accelerator, diluents, preservatives, colorants, flavors, correctives, stabilizers, humectants, antiseptics, antioxidant, or the like.

Examples of the parentarnal administration include injection (for example, subcutaneous injection or intravenous injection), rectal administration, or the like. Among these, injections are preferred.

For example, in preparing the injections, an aqueous solvent such as a normal saline solution or Ringer solution, non-aqueous solutions such as plant oil or fatty acid ester, a tonicity agent such as glucose or sodium chloride, a solubility assisting agent, a stabilizing agent, an antiseptic agent, a suspending agent, or an emulsifying agent, may be optionally used, in addition to the active ingredient.

Further, the medicine of the present invention may be administered by means of sustained-release formulation using sustained-release polymer. For example, the pharmaceutical composition of the present invention is introduced into a pellet of ethylene vinyl acetate polymer, and then the pellet can be surgically implanted into a tissue to be treated or prevented.

The medicine may contain, but is not limited to, 0.01 to 99% by weight, preferably 0.1 to 80% by weight, of the active ingredient.

A dose of the medicine of the present invention may be appropriately determined in accordance with, for example, age, sex, body weight, or degree of symptom of each patient, the type of each active ingredient, type of each disease, route of administration, or the like, and the determined dosage can be administered orally or parenterally.

In addition, a dosage form for administration of the medicine of the present invention is not limited to a drug medicine. That is, it can be administered as food and drink in various forms, such as functional food, healthy food (including drink), or animal food.

[4] Method for Treating or Preventing Mitochondrial Genetic Disease

A method for treating or preventing mitochondrial genetic disease of the present invention comprises administering to a subject in need of treating mitochondrial genetic disease the polyamide compound in an amount effective therefor. The administered polyamide is not particularly limited, so long as it is the polyamide compound described in the above paragraph "[1] Polyamide compound". The all-polyamide compound as mentioned above may be used. In the treating or preventing methods of the present invention, one or more polyamide compounds may be administered.

As the mitochondrial genetic disease, there may be mentioned a mitochondrial genetic disease caused by the A3236G mutation, Mitochondrial genetic diseases caused by the A3243G mutation, mitochondrial genetic diseases caused by the A3243T mutation, a mitochondrial genetic disease caused by the G3244A mutation, a mitochondrial genetic disease caused by the G3249A mutation, mitochondrial genetic diseases caused by the T3250C mutation, a mitochondrial genetic disease caused by the A3251G mutation, a mitochondrial genetic disease caused by the A3252G mutation, a mitochondrial genetic disease caused by the C3254A mutation, a mitochondrial genetic disease caused by the C3254G mutation, a mitochondrial genetic disease caused by the G3255A mutation, mitochondrial genetic diseases caused by the C3256T mutation, mitochondrial genetic diseases caused by the T3258C mutation, mitochondrial genetic diseases caused by the A3260G mutation. The appropriate polyamide composition described in the paragraph "[3] Pharmaceutical composition" can be selected and used according to each mutation.

[5] Polyamide Compound for Treating or Preventing Mitochondrial Genetic Disease

A polyamide compound for treating or preventing mitochondrial genetic disease of the present invention is only used for treating mitochondrial genetic disease. The polyamide compound for treating or preventing mitochondrial genetic disease of the present invention is not particularly limited, so long as it is the polyamide compound described in the above paragraph "[1] Polyamide compound". The all-polyamide compound as mentioned above may be used. One polyamide compound or a combination of two or more polyamide compounds for treating or preventing mitochondrial genetic disease of the present invention may be administered to mitochondrial genetic disease patients.

As for the mitochondrial genetic diseases, there may be mentioned a mitochondrial genetic disease caused by the A3236G mutation, mitochondrial genetic diseases caused by the A3243G mutation, mitochondrial genetic diseases caused by the A3243T mutation, a mitochondrial genetic disease caused by the G3244A mutation, a mitochondrial genetic disease caused by the G3249A mutation, mitochondrial genetic diseases caused by the T3250C mutation, a mitochondrial genetic disease caused by the A3251G mutation, a mitochondrial genetic disease caused by the A3252G mutation, a mitochondrial genetic disease caused by the C3254A mutation, a mitochondrial genetic disease caused by the C3254G mutation, a mitochondrial genetic disease caused by the G3255A mutation, mitochondrial genetic diseases caused by the C3256T mutation, mitochondrial genetic diseases caused by the T3258C mutation, mitochondrial genetic diseases caused by the A3260G mutation. The appropriate polyamide composition described in the paragraph "[3] Pharmaceutical composition" can be selected and used according to each mutation.

[5] Use for Preparing Medicine for Treating or Preventing Mitochondrial Genetic Disease One use of the present invention is preparing a medicine for treating or preventing mitochondrial genetic disease. The polyamide compound used is not particularly limited, so long as it is the polyamide compound described in the above paragraph "[1] Polyamide compound". The all-polyamide compound as mentioned above may be used. In the preparation of medicine for treating or preventing mitochondrial genetic disease, one or more polyamide compounds may be used.

As for the mitochondrial genetic diseases, there may be mentioned a mitochondrial genetic disease caused by the A3236G mutation, mitochondrial genetic diseases caused by the A3243G mutation, mitochondrial genetic diseases caused by the A3243T mutation, a mitochondrial genetic disease caused by the G3244A mutation, a mitochondrial genetic disease caused by the G3249A mutation, mitochondrial genetic diseases caused by the T3250C mutation, mitochondrial genetic diseases caused by the A3251G mutation, a mitochondrial genetic disease caused by the A3252G mutation, a mitochondrial genetic disease caused by the C3254A mutation, a mitochondrial genetic disease caused by the C3254G mutation, a mitochondrial genetic disease caused by the G3255A mutation, mitochondrial genetic diseases caused by the C3256T mutation, mitochondrial genetic diseases caused by the T3258C mutation, mitochondrial genetic diseases caused by the A3260G mutation. The appropriate polyamide composition described in the paragraph "[3] Pharmaceutical composition" can be selected according to each mutation, and used to prepare medicine for preventing or treating mitochondrial genetic disease.

<<Mechanism of Increase of Wild-Type mtDNA>>

The target double-stranded DNA corresponds to the base sequence of 3236th to 3260th in mtDNA, and is present on the mitochondria tRNA$^{Leu(UUR)}$ gene. The polyamide compound of the present invention is designed according to the base sequence of the wild-type mtDNA. Therefore, it is presumed that the polyamide compound of the present invention binds to the wild-type mtDNA selectively, in the statement where the wild-type mtDNA and the mutant mtDNA coexist. That is, the polyamide compound of the present invention may selectively bind to the wild-type mtDNA compared to the mutant mtDNA. Therefore, it is presumed that the polyamide compound can promote the replication of the wild-type mtDNA. In connection with this, it is known that a protein called mTERF (mitochondrial transcription termination factor) binds to a region of the sequence position of 3229th to 3256th in mt DNA. A mechanism for promoting the replication of the wild-type mtDNA by the polyamide compound of the present invention is not limited. However, it is presumed that the polyamide compound inhibits the binding of mTERF to the wild-type mtDNA.

Therefore, an effect of the present invention can be obtained by using compounds which bind to a nucleotide of a base sequence of 3236th to 3260th or 3229th to 3256th in mtDNA, instead of the polyamide compound of the present invention. As for the compound which may bind to the above nucleotides (hereinafter, referred to as a nucleotide binding compound) other than the polyamide compound, there may be mentioned, for example, PNA or low-molecular compound. The polyamide compound of the present invention does not bind to the mutant mtDNA, but binds to the wild-type mtDNA. If the PNA or the low-molecular compound does not bind to the mutant mtDNA and binds to the wild-type mtDNA, the same effect as the polyamide compound of the present invention can be obtained. A length of nucleotide region to which the nucleotide binding compound binds, is not limited, so long as it is 3 or more nucleotides, but preferably 4 or more nucleotides, more preferably 5 or more nucleotides, further preferably 6 or more nucleotides.

The advantageous effects of the polyamide compound of the present invention are shown in the replication of the wild-type mtDNA, the double-stranded DNA having a base sequence of 3236th to 3260th or 3229th to 3256th in mtDNA, and competing with the mutant mtDNA. That is, the above effects are not shown in a polyamide compound binding to the wild-type mtDNA of other region which has the mutant mtDNA. In other words, the polyamide compound of the present invention selectively binds to the wild-type mtDNA having a base sequence of 3236th to 3260th in mtDNA, as a result, the replication rate of the wild-type mtDNA may be increased compared to one of the mutant mtDNA.

(Cytotoxicity of Polyamide Compound)

In order to use a compound for treating diseases, it is important that the compound has no adverse effects on a subject (human or animals other than human) in need of an administration of the compound. As shown in Example 4, the polyamide compound of the present invention was not cytotoxic to 143B cells and HeLa cells. Therefore, it is presumed that the agent for promoting replication of wild-type mtDNA, or the pharmaceutical composition of the present invention has no side effects on human or the like.

The nucleotide sequence of the target double-stranded DNA wherein the polyamide compound of the present invention binds overlaps with the mTERF-binding nucleotide sequence of 28 bp. It is presumed that mTERF binds to 28 bp of nucleotide sequence present near the boundary of 16S rRNA and tRNA$^{Leu(UUR)}$, and relates to a transcription termination thereof. A main function of mTERF is thought to efficiently synthesize mitochondrial rRNAs. The binding region of the polyamide compound of the present invention overlaps with the binding region of mTERF, and therefore, it is considered that the polyamide compound inhibits the function (i.e. synthesis of mitochondrial rRNAs) of mTERF, and has adverse effects on cells. However, the polyamide compound of the present invention is not cytotoxic, and thus it is presumed that the agent for promoting replication of the wild-type mtDNA or the pharmaceutical composition of the present invention does not lead to side effects.

EXAMPLES

The present invention now will be further illustrated by, but is by no means limited to, the following Examples.

Example 1

In this Example, an ML1 polyamide was produced in accordance with an Fmoc method by a solid-phase synthesis. The ML1 polyamide has the follow sequence: Ac-Py-Py-Py-β-Im-Py-Py-γ-Im-Im-Py-β-Im-Py-Im-β-Dp.

In the synthesis, NovaPEG Wang Resin was used as a solid-phase, and Py(N-methylpyrrole), Im(N-methylimidazole), β-alanine, or γ-aminobutyric acid was sequentially added by dehydration condensation (amide binding), and a chain was extended. Finally, N,N-dimethyl-1,3-propanediamine was added, and the whole was removed from the solid-phase surface around 60'C to obtain a polyamide compound. A molecular weight of the resulting polyamide compound was confirmed by a mass spectroscope (Shimadzu Corporation).

The resulting ML1 polyamide was purified by elution from 0.1% acetate/acetonitrile gradient in reverse phase chromatography (Prominence/LC solution, Shimadzu Corporation). The resulting ML1 polyamide was lyophilized in a vacuum by FDU-1200 (Tokyo Rikakikai Co., Ltd.; EYELA) to remove solvent. A light yellow or white-powdered solid was obtained.

The ML1 polyamide was dissolved in ddH$_2$O or 50% DMSO solution and the solutions were used in the subsequent Examples.

The powdered polyamide was dissolved in ddH$_2$O or 50% DMSO aqueous solution, and the absorbance of the ML1 polyamide solution at the maximum absorption wavelength was measured by a spectrophotometer (light path length=1 cm). The concentration (M) of the ML1 polyamide can be calculated from the absorbance in accordance with the following equations:

<When the solvent is ddH$_2$O>

Concentration (M)=Absorbance/[8600×12]

<When the solvent is DMSO, or DMF>

Concentration (M)=Absorbance/[9800×12]

Example 2

In this Example, a binding specific to the base sequence was confirmed in vitro between the ML1 polyamide and the target. The assay was carried out in EMSA (electrophoretic mobility shift assay). The wild-type oligo-DNA with 21 bases containing the 3243rd base on which the A3243G mutation exists and the A3243G mutation oligo-DNA thereof were produced. A sense-stranded DNA with FITC bound at 5'-end and an antisense-stranded DNA were thermally denatured, slowly cooled, and annealed to obtain dsDNAs having the following sequence:

```
<Normal (wild-type)mtDNA template>
                         SEQ ID NOs: 23 and 24
5'-FITC-TGTTAAAGATGGCAGAGCCCG-3'

3'-ACAATTTCTACCGTCTCGGGC-5'

<A3243G mutation mtDNA template>
                         SEQ ID NOs: 25 and 26
5'-FITC-TGTTAAAGATGGCAGGGCCCG-3'

3'-ACAATTTCTACCGTCCCGGGC-5'
```

The underlined portions are recognition domains of the MLI polyamide.

To dsDNA (50 pmol/10 μL), 40 μL of ddH$_2$O was added and the whole was diluted to 1 pmol/μL. 4 pmol of the resulting dsDNA were mixed with the MLI polyamide solution so that the concentration became 10$^{-4}$M, and incubated for 1 hour at 37° C. Then, the sample was mixed with a loading buffer and applied on 20% non-denatured acrylamide gel (0.5×TBE) which was pre-run for 10 minutes at 350 V. An electrophoresis was carried out at 4'C and 100 V until BPB reached ¾ of the lower end of the gel, and a shift of the band was detected by LAS-3000 (Fuji Film).

The composition of the non-denatured acrylamide gel used in EMSA is shown as below:

| <Composition of EMSA gel> | |
|---|---|
| 30% acrylamide | 16.5 mL |
| 10XTBE | 2.5 mL |
| 10% APS | 188 μL |
| glycerol | 878 μL |
| ddH$_2$O | 14.0 mL |
| TEMED | 11.3 μL |
| | 25.0 mL |

Figure 3:
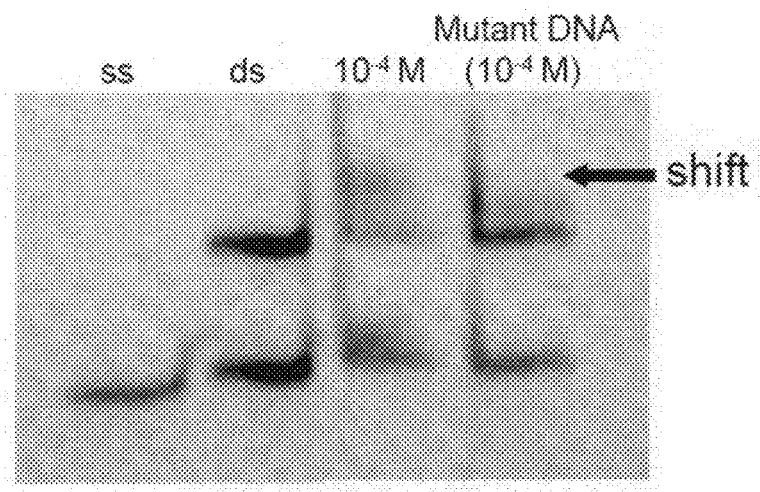
FIG. 3 is a photograph showing an EMSA analysis of base sequence-specific binding of ML1 polyamide to a target sequence. In a sequence of the wild-type mtDNA, a band of dsDNA was significantly shifted. On the other hand, in the A3243G mutant dsDNA having one point mutation, there is no significant shift of a band thereof. These results indicate that the ML1 polyamide binds to the wild-type mtDNA, nucleotide sequence-specifically, in vitro.

As illustrated in FIG. 3, there is a clear shift of the band due to the binding of the MLI polyamide and the wild-type dsDNA at $10^{-4}$ M MLI polyamide. This experimental data shows that the MLI polyamide rapidly and firmly bonds to the target dsDNA in vitro. Further, a shift of the band due to the bonding of the MLI polyamide and the mutant dsDNA was not clearly observed at the concentration ($10^{-4}$ M) where the shift due to the binding of the dsDNA having the target sequence was observed. This means that the MLI polyamide can recognize a one-base difference, and actually bound to the specific base sequence in vitro.

Example 3

In this Example, the effect of facilitating replication of wild-type mtDNAs by the MLI polyamide in cells was confirmed.

The MLI polyamide was given to the cultivated MELAS cybrid cells to confirm if the wild-type mtDNAs were positively reproduced in cells.

2SD cybrid cells were seeded on a 10 cm dish, and the MLI polyamide dissolved in 50% DMSO was added to the complete DMEM so that a final concentration thereof became 1 µM, 5 µM, or 10 µM. The medium to which the MLI polyamide was added was replaced every third day. In the control experiments, DMSO with the same diluted rate was added to the medium. The polyamide solution in 50% DMSO solution was diluted with ddH$_2$O so that the concentration of DMSO in the medium became 0.1% or less, or 0.05% at a maximum.

Total DNAs were extracted from the cybrid cells treated by the MLI polyamide 14 days later, PCR-RFLP was then carried out, the bands were quantitatively analyzed by microchip electrophoresis (MCE-202 MultiNA; Shimadzu Corporation), and a mutation rate of the cybrid cells was analyzed.

Figure 4:
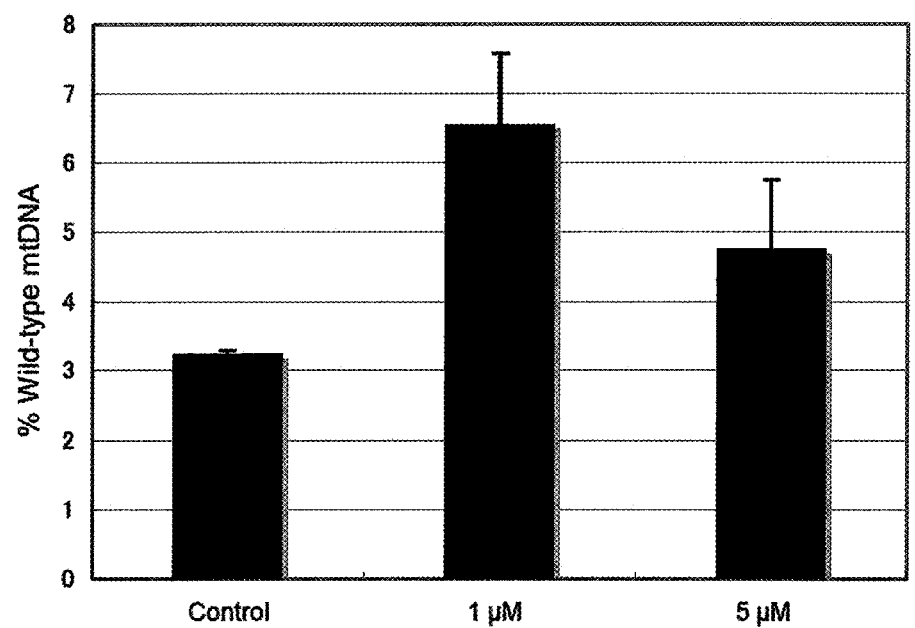
FIG. 4 is a graph showing that the amount of the wild-type DNA of cybrid cells (14 days after) after PCR-RFLP, was analyzed using a device for quantitative determination by electrophoresis (mean±S.E.M. n=3). In the living cells, increase levels of wild-type mtDNA by ML1 polyamide were observed in 1 μM and 5 μM of ML1 polyamide concentration.

As a result, a concentration-dependent increase level of the wild-type mtDNAs was clearly observed in the cybrid cells treated by the MLI polyamide for 14 days. Namely, the decrease of the mutation rate was observed at 1 µM or 5 µM, accompanied by the increase of the replication of the normal (wild-type) mtDNAs (see FIG. 4).

Further, long-term effects were analyzed when the concentration of the MLI polyamide in the medium was 1 µM, 500 nM, or 100 nM. Total DNAs were extracted from the cybrid cells 7 days, 15 days, or 35 days later, PCR-RFLP was then carried out, electrophoresis was performed on 2% agarose gel (1×TAE), and an increase level of the wild-type mtDNAs was measured.

Figure 5:
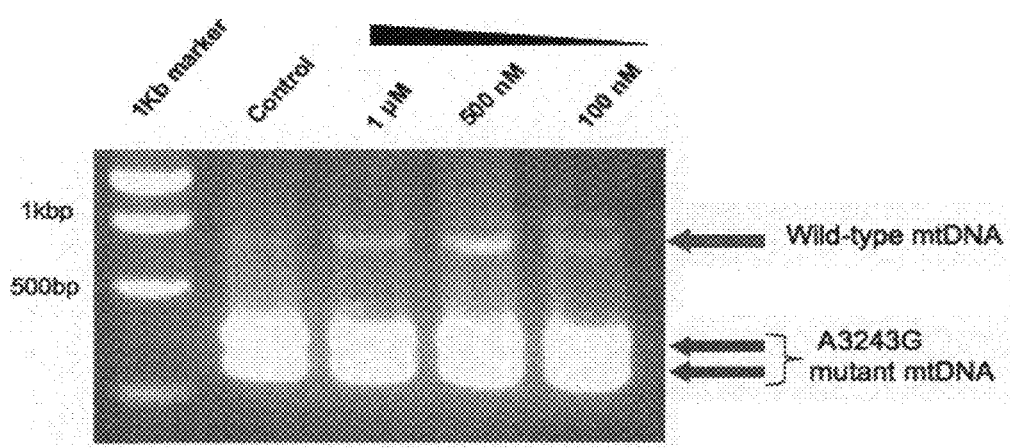
FIG. 5 is a photograph showing an increase level of wild-type mtDNA in cybrid cells treated with ML1 polyamide for 15 days. A significant increase level of wild-type mtDNA was observed in cybrid cells treated with 500 nM of ML1 polyamide.

As a result, a grossly visible increase level of the wild-type mtDNAs was confirmed in all cells treated at the concentration of 1 µM, 500 nM, or 100 nM, and electrophoresis on agarose gel after PCR-RFLP, in comparison with control. FIG. 5 shows the increase of the wild-type mtDNAs after 15 days.

Figure 6:
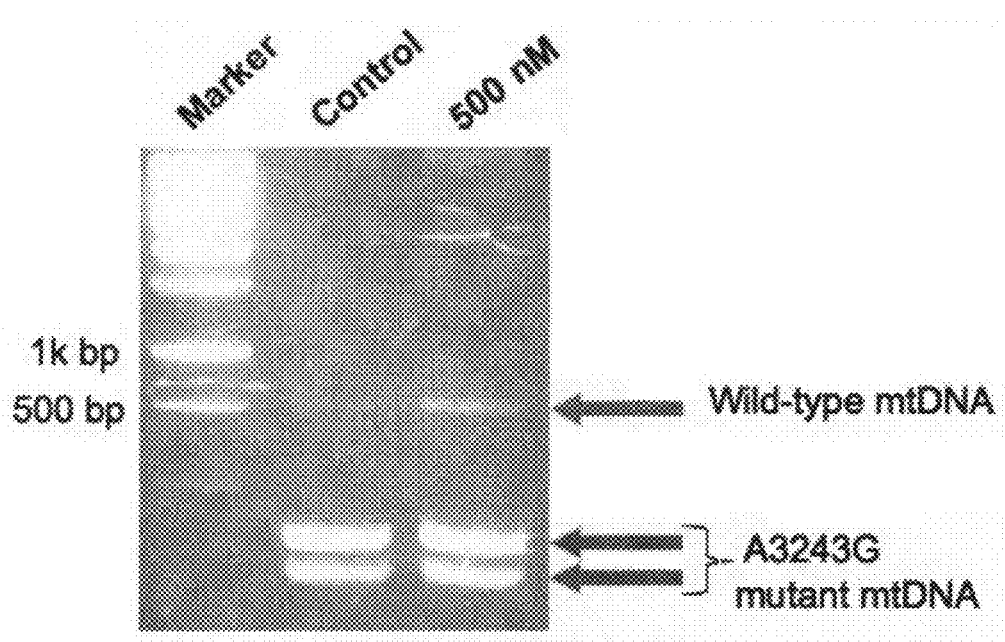
FIG. 6 is a photograph showing an mtDNA composition in the 2SD cybrid cells treated with ML1 polyamide for 35 days. In the control cells, there are very few wild-type mtDNA. However, in the 2SD cybrid cells, a band amplified by a continuous increase level of wild-type mtDNA can be confirmed.

Further, 2SD cybrid cells were cultivated for 35 days at 500 nM of the MLI polyamide, and a continuous increase of the wild-type mtDNAs was observed (see FIG. 6).

Example 4

In this Example, cytotoxicity of the MLI polyamide was examined so as to confirm the side effects of the pharmaceutical composition and so on according to the present invention.

143B cells or HeLa cells were cultured in a medium prepared by adding 1 µM of ML1 polyamide to a 10% FBS-added DMEM (free of sodium pyruvate and uridine) wherein respiratory chain-defective cells are inviable. The synthesis of the respiratory chain proteins in mitochondria is essential to life-support, and only a slight dysfunction thereof results in cell death.

143B cells or HeLa cells were cultured for a week in normal DMEM, complete DMEM (containing 0.1 mg/mL of sodium pyruvate, and 50 µg/mL of uridine), complete DMEM with the ML1 polyamide, or DMEM with the ML1 polyamide, and survival or death was observed.

Figure 7:
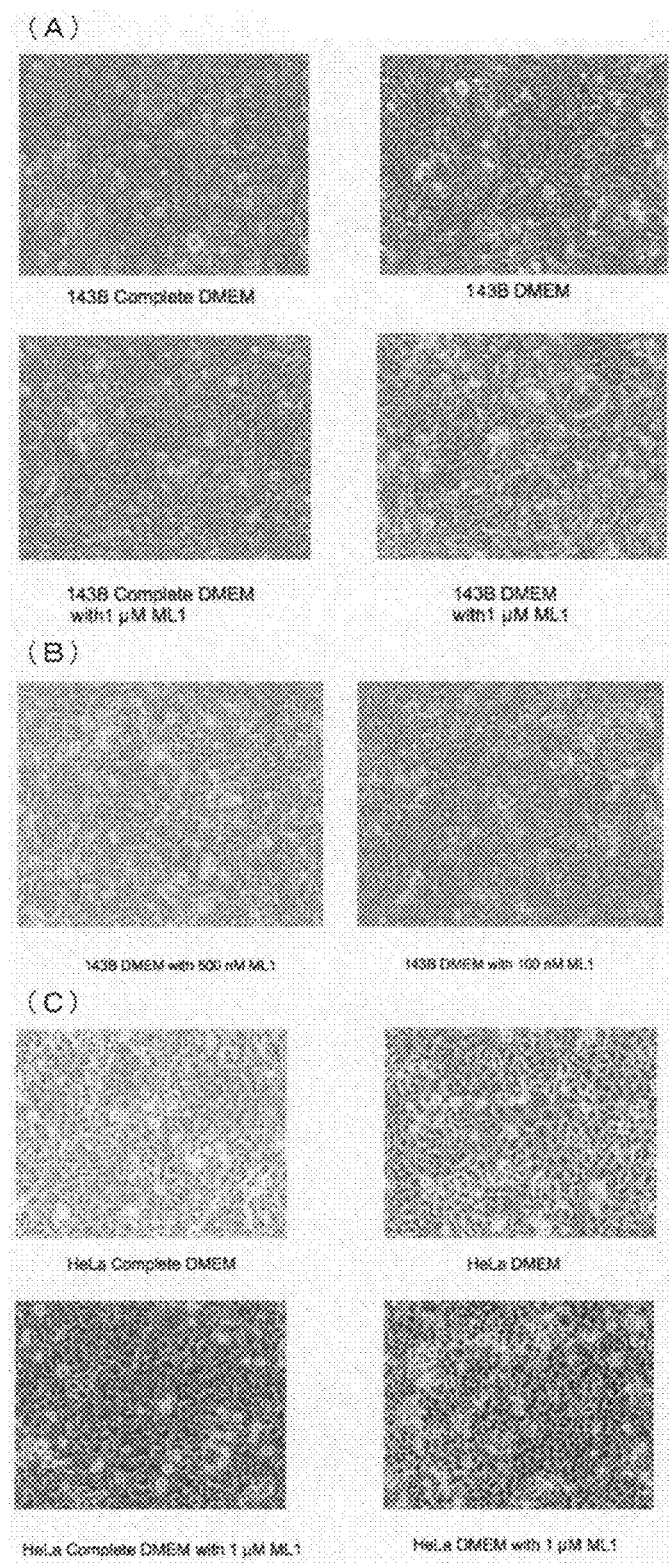

In the culture of 143B cells, the MLI polyamide was added at the concentration of 100 nM, 500 nM, or 1 µM, whereas in the culture of Hela cells, the MLI polyamide was added at the concentration of 1 µM. FIG. 7 shows 143B cells with 1 µM addition (FIG. 7A), 143B cells with 500 nM or 100 nM addition (FIG. 7B), and Hela cells with 1 µM addition (FIG. 7C) after 30 hours from the start of the culture. 143B cells or HeLa cells cultured in DMEM without uridine and sodium pyruvate did not show any morphological changes or cell cytotoxicity after culture for 30 hours or 1 week further.

INDUSTRIAL APPLICABILITY

The polyamide compound according to the present invention can be used as an effective ingredient of an agent for promoting replication of a wild-type mtDNA or a pharmaceutical composition for treating a mitochondrial genetic disease. A mitochondrial genetic disease can be treated or prevented by the present agent for promoting replication of the wild-type mtDNA or the present pharmaceutical composition for treating a mitochondrial genetic disease. In particular, the pharmaceutical composition according to the present invention can treat or prevent a mitochondrial genetic disease caused by at least one mutation selected from the group consisting of the A3236G mutation, the A3243G mutation, the A3243T mutation, the G3244A mutation, the G3249A mutation, the T3250C mutation, the A3251G mutation, A3252G mutation, the C3254A mutation, the C3254G mutation, the G3255A mutation, the C3256T mutation, the T3258C mutation, and the A3260G mutation.

Although the present invention has been described with reference to specific embodiments, various changes and modifications obvious to those skilled in the art are possible without departing from the scope of the appended claims.

The invention claimed is:

1. A pharmaceutical composition characterized by comprising an active ingredient wherein the active ingredient is a polyamide compound, or a pharmaceutically acceptable salt thereof, binding to a target double-stranded DNA, wherein said target double-stranded DNA comprises at least one nucleotide pair selected from the group consisting of an A/T pair consisting of the first A of the following sense-stranded DNA and the corresponding T, an A/T pair consisting of the 8th A of the following sense-stranded DNA and the corresponding T, a G/C pair consisting of the 9th G of the following sense-stranded DNA and the corresponding C, a G/C pair consisting of the 14th G of the following sense-stranded DNA and the corresponding C, a T/A pair consisting of the 15th T of the following sense-stranded DNA and the corresponding A, an A/T pair consisting of the 16th A of the following sense-stranded DNA and the corresponding T, an A/T pair consisting of the 17th A of the following sense-stranded DNA and the corresponding T, a C/G pair consisting of the 19th C of the following sense-stranded DNA and the corresponding G, a G/C pair consisting of the 20th G of the following sense-stranded DNA and the corresponding C, a C/G pair consisting of the 21st C of the following sense-stranded DNA and the corresponding G, a T/A pair consisting of the 23rd T of the following sense-stranded DNA and the corresponding A, an A/T pair consisting of the 25th A of the following sense-stranded DNA and the corresponding T, in the double stranded DNA of the following formula(1):

```
[Chem. 1]
5'-ATGGCAGAGCCCGGTAATCGCATAA-3'

3'-TACCGTCTCGGGCCATTAGCGTATT-5'         (1)
``` which consists of the sense-stranded DNA having a base sequence of 5'-ATGGCAGAGCCCGGTAATCGCATAA-3' (SEQ ID NO: 1) and the antisense-stranded DNA having a base sequence of 5'-TTATGCGATTACCGGGCTCTGCCAT-3' (SEQ ID NO: 2); and at least one end of said target double-stranded DNA is an A/T or T/A pair;

(1) a residue of the polyamide compound, corresponding to the A/T pair or T/A pair at one end thereof is a turn structure selected from the group consisting of γ-aminobutyric acid residue, (R)2,4-diaminobutyric acid residue, and 5-aminovaleric acid residue, wherein the hydrogen atom of the residues may be substituted with an alkyl group having 1 to 4 carbon atoms, an amino group, a hydroxyl group, a carboxyl group, or —NH3;

(2) the binding region of the polyamide compound, corresponding to the target double-stranded DNA except for the A/T pair or T/A pair at one end thereof, is composed of (a) Im/Py, or Im/β, corresponding to the G/C pair of the target double-stranded DNA, (b) Py/Im, or β/Im, corresponding to the C/G pair of the target double-stranded DNA, (c) Py/Py, Py/Hp, Py/β, β/Py, or β/β corresponding to the A/T pair of the target double-stranded DNA, and (d) Py/Py, Hp/Py, Py/β, β/Py, or β/β, corresponding to the T/A pair of the target double-stranded DNA, (wherein Im is N-methylimidazole, Py is N-methylpyrrole, Hp is 3-hydroxy-N-methylpyrrole, and β is β-alanine; and Im/β corresponding to the G/C pair and β/Im corresponding to the C/G pair can be only used in the case of a successive Im•β/Im•β corresponding to a successive G•C/G•C pair or a successive β•Im/β•Im corresponding to a successive C•G/C•G pair; and the hydrogen atom of the Im residue, Py residue, Hp residue, or β residue may be substituted to an alkyl group having 1 to 4 carbon atoms, an amino group, a hydroxyl group, a carboxyl group, or —NH3), and the binding region comprises at least one residue pair of Im/β corresponding to the G/C pair, β/Im corresponding to the C/G pair, β/β corresponding to the A/T pair, or β/β corresponding to the T/A pair, of the target double stranded DNA;

(3) an end of the polyamide compound corresponding to the 5' end of the other end of the target double-stranded DNA is an amino group of Im residue, an amino group of Py residue, an amino group of Hp residue, an amino group of β-alanine, a hydrogen atom, an alkyl group having 1 to 4 carbon atoms, a hydroxyl group, a carboxyl group, or an acyl group having 1 to 4 carbon atoms; an end of the polyamide compound corresponding to the 3' end of the other end of the target double-stranded DNA is a carboxyl group of Im residue, a carboxyl group of Py residue, a carboxyl group of Hp residue, a carboxyl group of β-alanine, an N,N-dimethylaminopropyl residue, or a β-alanine•N,N-dimethylaminopropyl residue.

2. A pharmaceutical composition according to claim 1, wherein the pharmaceutical composition is for treating or preventing sporadic bilateral optic neuropathy with an A3236G mutation, and the active ingredient has a residue corresponding to an A/T pair consisting of the first A of the sense-stranded DNA 5'-ATGGCAGAGCCCGGTAATCGCATAA-3' (SEQ ID NO: 1) and the corresponding T.

3. A pharmaceutical composition according to claim 1, wherein the pharmaceutical composition is for treating or preventing mitochondrial myopathy, encephalopathy, lactic acidosis, stroke-like episodes; diabetes and hypacusia; mitochondrial myopathy; Leigh's syndrome; sensory deafness; chronic progressive external ophthalmoplegia; diabetes with matricliny hypacusia; or focal segmental glomerulosclerosis, with an A3243G mutation, and the active ingredient has a residue corresponding to an A/T pair consisting of the 8th A of the sense-stranded DNA 5'-ATGGCAGAGCCCGG-TAATCGCATAA-3' (SEQ ID NO: 1) and the corresponding T.

4. A pharmaceutical composition according to claim 1, wherein the pharmaceutical composition is for treating or preventing mitochondrial myopathy, encephalopathy, lactic acidosis, stroke-like episodes; mitochondrial myopathy; sensory deafness; or chronic progressive external ophthalmoplegia, with an A3243T mutation, and the active ingredient has a residue corresponding to an A/T pair consisting of the 8th A of the sense-stranded DNA 5'-ATGGCAGAGC-CCGGTAATCGCATAA-3' (SEQ ID NO: 1) and the corresponding T, and the residue corresponding to T of the A/T pair is Hp residue.

5. A pharmaceutical composition according to claim 1, wherein the pharmaceutical composition is for treating or preventing mitochondrial myopathy, encephalopathy, lactic acidosis, stroke-like episodes with a G3244A mutation, and the active ingredient has a residue corresponding to a G/C pair consisting of the 9th G of the sense-stranded DNA 5'-ATGGCAGAGCCCGGTAATCGCATAA-3' (SEQ ID NO: 1) and the corresponding C.

6. A pharmaceutical composition according to claim 1, wherein the pharmaceutical composition is for treating or preventing Kearns-Sayre syndrome with a G3249A mutation, and the active ingredient has a residue corresponding to a G/C pair consisting of the 14th G of the sense-stranded DNA 5'-ATGGCAGAGCCCGGTAATCGCATAA-3' (SEQ ID NO: 1) and the corresponding C.

7. A pharmaceutical composition according to claim 1, wherein the pharmaceutical composition is for treating or preventing mitochondrial myopathy, or chronic progressive external ophthalmoplegia with a T3250C mutation, and the active ingredient has a residue corresponding to a T/A pair consisting of the 15th T of the sense-stranded DNA 5'-ATG-GCAGAGCCCGGTAATCGCATAA-3' (SEQ ID NO: 1) and the corresponding A.

8. A pharmaceutical composition according to claim 1, wherein the pharmaceutical composition is for treating or preventing mitochondrial myopathy with an A3251G mutation, and the active ingredient has a residue corresponding to a A/T pair consisting of the 16th A of the sense-stranded DNA 5'-ATGGCAGAGCCCGGTAATCGCATAA-3' (SEQ ID NO: 1) and the corresponding T.

9. A pharmaceutical composition according to claim 1, wherein the pharmaceutical composition is for treating or preventing mitochondrial myopathy, encephalopathy, lactic acidosis, stroke-like episodes with an A3252G mutation, and the active ingredient has a residue corresponding to a A/T pair consisting of the 17th A of the sense-stranded DNA 5'-ATGGCAGAGCCCGGTAATCGCATAA-3' (SEQ ID NO: 1) and the corresponding T.

10. A pharmaceutical composition according to claim 1, wherein the pharmaceutical composition is for treating or preventing diabetes in pregnancy with a C3254A mutation, or mitochondrial myopathy with a C3254G mutation, and the active ingredient has a residue corresponding to a C/G pair consisting of the 19th C of the sense-stranded DNA 5'-ATGGCAGAGCCCGGTAATCGCATAA-3' (SEQ ID NO: 1) and the corresponding G.

11. A pharmaceutical composition according to claim 1, wherein the pharmaceutical composition is for treating or preventing MERRF/KSS overlap syndrome with a G3255A mutation, and the active ingredient has a residue corresponding to a G/C pair consisting of the 20th G of the sense-stranded DNA 5'-ATGGCAGAGCCCGGTAATCGCATAA-3' (SEQ ID NO: 1) and the corresponding C.

12. A pharmaceutical composition according to claim 1, wherein the pharmaceutical composition is for treating or preventing mitochondrial myopathy, encephalopathy, lactic acidosis, stroke-like episodes/myoclonic epilepsy with ragged-red fibers with a C3256T mutation, and the active ingredient has a residue corresponding to a C/G pair consisting of the 21st C of the sense-stranded DNA 5'-ATG-GCAGAGCCCGGTAATCGCATAA-3' (SEQ ID NO: 1) and the corresponding G.

13. A pharmaceutical composition according to claim 1, wherein the pharmaceutical composition is for treating or preventing mitochondrial myopathy, encephalopathy, lactic acidosis, stroke-like episodes/myopathy with a T3258C mutation, and the active ingredient has a residue corresponding to a T/A pair consisting of the 23rd T of the sense-stranded DNA 5'-ATGGCAGAGCCCGGTAATCGCATAA-3' (SEQ ID NO: 1) and the corresponding A.

14. A pharmaceutical composition according to claim 1, wherein the pharmaceutical composition is for treating or preventing adult matricliny myopathy and cardiac myopathy with an A3260G mutation, and the active ingredient has a residue corresponding to a A/T pair consisting of the 25th A of the sense-stranded DNA 5'-ATGGCAGAGCCCGG-TAATCGCATAA-3' (SEQ ID NO: 1) and the corresponding T, or a pharmaceutically acceptable salt thereof, as an active ingredient.

* * * * *

SEQUENCE LISTING

<160> NUMBER OF SEQ ID NOS: 26

<210> SEQ ID NO 1
<211> LENGTH: 25
<212> TYPE: DNA
<213> ORGANISM: Homo sapiens

```
<400> SEQUENCE: 1
atggcagagc ccggtaatcg cataa                                          25

<210> SEQ ID NO 2
<211> LENGTH: 25
<212> TYPE: DNA
<213> ORGANISM: Homo sapiens

<400> SEQUENCE: 2
ttatgcgatt accgggctct gccat                                          25

<210> SEQ ID NO 3
<211> LENGTH: 8
<212> TYPE: DNA
<213> ORGANISM: Homo sapiens

<400> SEQUENCE: 3 tggcagag                                                              8

<210> SEQ ID NO 4
<211> LENGTH: 11
<212> TYPE: DNA
<213> ORGANISM: Homo sapiens

<400> SEQUENCE: 4
tggcagagcc c                                                         11

<210> SEQ ID NO 5
<211> LENGTH: 12
<212> TYPE: DNA
<213> ORGANISM: Homo sapiens

<400> SEQUENCE: 5
tggcagagcc cg                                                        12

<210> SEQ ID NO 6
<211> LENGTH: 8
<212> TYPE: DNA
<213> ORGANISM: Homo sapiens

<400> SEQUENCE: 6 agcccggt                                                              8

<210> SEQ ID NO 7
<211> LENGTH: 9
<212> TYPE: DNA
<213> ORGANISM: Homo sapiens

<400> SEQUENCE: 7 agcccggta                                                             9

<210> SEQ ID NO 8
<211> LENGTH: 7
<212> TYPE: DNA
<213> ORGANISM: Homo sapiens

<400> SEQUENCE: 8 tggcaga                                                               7

<210> SEQ ID NO 9
<211> LENGTH: 8
<212> TYPE: DNA
<213> ORGANISM: Homo sapiens
```

```
<400> SEQUENCE: 9 atggcaga                                                               8

<210> SEQ ID NO 10
<211> LENGTH: 9
<212> TYPE: DNA
<213> ORGANISM: Homo sapiens

<400> SEQUENCE: 10 taatcgcat                                                              9

<210> SEQ ID NO 11
<211> LENGTH: 9
<212> TYPE: DNA
<213> ORGANISM: Homo sapiens

<400> SEQUENCE: 11 aatcgcata                                                              9

<210> SEQ ID NO 12
<211> LENGTH: 8
<212> TYPE: DNA
<213> ORGANISM: Homo sapiens

<400> SEQUENCE: 12 tcgcataa                                                               8

<210> SEQ ID NO 13
<211> LENGTH: 8
<212> TYPE: DNA
<213> ORGANISM: Homo sapiens

<400> SEQUENCE: 13 ctctgcca                                                               8

<210> SEQ ID NO 14
<211> LENGTH: 11
<212> TYPE: DNA
<213> ORGANISM: Homo sapiens

<400> SEQUENCE: 14
gggctctgcc a                                                          11

<210> SEQ ID NO 15
<211> LENGTH: 12
<212> TYPE: DNA
<213> ORGANISM: Homo sapiens

<400> SEQUENCE: 15
cgggctctgc ca                                                         12

<210> SEQ ID NO 16
<211> LENGTH: 8
<212> TYPE: DNA
<213> ORGANISM: Homo sapiens

<400> SEQUENCE: 16 accgggct                                                               8

<210> SEQ ID NO 17
<211> LENGTH: 9
<212> TYPE: DNA
```

```
<213> ORGANISM: Homo sapiens

<400> SEQUENCE: 17 taccgggct                                                                9

<210> SEQ ID NO 18
<211> LENGTH: 7
<212> TYPE: DNA
<213> ORGANISM: Homo sapiens

<400> SEQUENCE: 18 tctgcca                                                                  7

<210> SEQ ID NO 19
<211> LENGTH: 8
<212> TYPE: DNA
<213> ORGANISM: Homo sapiens

<400> SEQUENCE: 19 tctgccat                                                                 8

<210> SEQ ID NO 20
<211> LENGTH: 9
<212> TYPE: DNA
<213> ORGANISM: Homo sapiens

<400> SEQUENCE: 20 atgcgatta                                                                9

<210> SEQ ID NO 21
<211> LENGTH: 9
<212> TYPE: DNA
<213> ORGANISM: Homo sapiens

<400> SEQUENCE: 21 tatgcgatt                                                                9

<210> SEQ ID NO 22
<211> LENGTH: 8
<212> TYPE: DNA
<213> ORGANISM: Homo sapiens

<400> SEQUENCE: 22 ttatgcga                                                                 8

<210> SEQ ID NO 23
<211> LENGTH: 21
<212> TYPE: DNA
<213> ORGANISM: Homo sapiens

<400> SEQUENCE: 23
tgttaaagat ggcagagccc g                                                 21

<210> SEQ ID NO 24
<211> LENGTH: 21
<212> TYPE: DNA
<213> ORGANISM: Homo sapiens

<400> SEQUENCE: 24
cgggctctgc catctttaac a                                                 21

<210> SEQ ID NO 25
<211> LENGTH: 21
```

```
<212> TYPE: DNA
<213> ORGANISM: Homo sapiens

<400> SEQUENCE: 25
tgttaaagat ggcagggccc g                                              21

<210> SEQ ID NO 26
<211> LENGTH: 21
<212> TYPE: DNA
<213> ORGANISM: Homo sapiens

<400> SEQUENCE: 26
cgggccctgc catctttaac a                                              21
```